(12) United States Patent
Hodgetts et al.

(10) Patent No.: US 6,943,173 B2
(45) Date of Patent: Sep. 13, 2005

(54) 5-SUBSTITUTED 2-ARYL-4-PYRIMIDINONES

(75) Inventors: Kevin J. Hodgetts, Killingworth, CT (US); Dario Doller, Wallingford, CT (US)

(73) Assignee: Neurogen Corporation, Branford, CT (US)

( * ) Notice: Subject to any disclaimer, the term of this patent is extended or adjusted under 35 U.S.C. 154(b) by 417 days.

(21) Appl. No.: 09/908,444

(22) Filed: Jul. 18, 2001

(65) Prior Publication Data

US 2002/0052387 A1 May 2, 2002

Related U.S. Application Data

(60) Provisional application No. 60/219,703, filed on Jul. 18, 2000.

(51) Int. Cl.[7] .................... C07D 239/36; A61K 31/505; A61K 31/506; A61P 3/12
(52) U.S. Cl. ................ 514/269; 544/314; 544/319
(58) Field of Search .................. 514/269; 544/314, 544/319

(56) References Cited

U.S. PATENT DOCUMENTS

| | | | | |
|---|---|---|---|---|
| 4,665,175 A | * | 5/1987 | Maurer ..................... | 544/243 |
| 4,686,290 A | * | 8/1987 | Maurer ..................... | 544/243 |
| 5,254,558 A | * | 10/1993 | Bernstein et al. ........... | 514/269 |
| 5,670,494 A | * | 9/1997 | Dolle et al. ................ | 514/86 |
| 5,861,380 A | | 1/1999 | Gyorkos et al. ............ | 514/19 |
| 5,948,785 A | * | 9/1999 | Akahoshi et al. .......... | 514/269 |
| 5,972,946 A | | 10/1999 | Murata et al. .............. | 514/31 |
| 6,001,814 A | | 12/1999 | Gyorkos et al. ............ | 514/18 |
| 6,121,202 A | * | 9/2000 | Karp et al. ................. | 504/242 |
| 2002/0058667 A1 | * | 5/2002 | Castelhano et al. ........ | 514/258 |

FOREIGN PATENT DOCUMENTS

| | | |
|---|---|---|
| DE | 1122533 * | 1/1962 |
| EP | 0 826 671 | 3/1998 |
| EP | 0 826 673 | 3/1998 |
| EP | 0 936 216 | 8/1999 |
| EP | 0 940 400 | 9/1999 |
| WO | 93/21210 | 10/1993 |
| WO | 93/21214 | 10/1993 |
| WO | 95/26958 * | 10/1995 |
| WO | 96/39400 | 12/1996 |
| WO | 97/14684 | 4/1997 |
| WO | 99/32459 | 7/1999 |
| WO | 99/36426 | 7/1999 |
| WO | 99/62518 * | 12/1999 |
| WO | 99/62538 | 12/1999 |

OTHER PUBLICATIONS

Hullar T.L. et al., "Pyridoxal Phosphate. III. Pyrimidine Analogs . . . " J. Med. Chem,, 1969, vol. 12, No. 3, pp. 424–426.*
Dolle et al., "First Examples of Peptidomimetic Inhibitors of Interleukin 1β Converting Enzyme", J. Med. Chem., vol. 39, pp. 2438–2440, 1996.*
Veale et. al., "Nonpeptidic Inhibitors of Human Leukocyte Elastase . . . ", J. Med. Chem., vol. 38, pp. 98–108, 1995.*

* cited by examiner

Primary Examiner—Venkataraman Balasubramanian
(74) Attorney, Agent, or Firm—Peter F. Corless; John B. Alexander; Edwards & Angell, LLP

(57) ABSTRACT

Arylpyrimidinone compounds that act as selective modulators of CRF 1 receptors are provided. These compounds are useful in the treatment of a number of CNS and periphereal disorders, particularly stress, anxiety, depression, cardiovascular disorders, and eating disorders. Methods of treatment of such disorders and well as packaged pharmaceutical compositions are also provided.

Compounds of the invention are also useful as probes for the localization of CRF receptors and as standards in assays for CRF receptor binding. Methods of using the compounds in receptor localization studies are given.

36 Claims, No Drawings

5-SUBSTITUTED 2-ARYL-4-PYRIMIDINONES

The present application claims the benefit of U.S. provisional application No. 60/219,703, filed Jul. 18, 2000, which is incorporated herein by reference in its entirety.

FIELD OF THE INVENTION

The present invention relates to novel arylpyrimidinone compounds that bind with high selectivity and/or high affinity to CRF receptors (Corticotropin Releasing Factor Receptors). This invention also relates to pharmaceutical compositions comprising such compounds and to the use of such compounds in treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. Additionally this invention relates to the use such compounds as probes for the localization of CRF receptors in cells and tissues. Preferred CRF receptors are CRF1 receptors.

BACKGROUND OF THE INVENTION

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

CRF has also been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15–1788, which was without behavioral activity alone in the operant conflict test, reversed the effects of CRF in a dose-dependent manner, while the benzodiazepine inverse agonist FG 7142 enhanced the actions of CRF.

CRF has also been implicated in the pathogeneisis of certain immunological, cardiovascular or heart-related diseases such as hypertension, tachycardia and congestive heart failure, stroke and osteoporosis, as well as in premature birth, psychosocial dwarfism, stress-induced fever, ulcer, diarrhea, post-operative ileus and colonic hypersensitivity associated with psychopathological disturbance and stress.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders. Of particular interest are that preliminary studies examining the effects of a CRF receptor antagonist peptide (α-helical $CRF_{9-41}$) in a variety of behavioral paradigms have demonstrated that the CRF antagonist produces "anxiolytic-like" effects qualitatively similar to the benzodiazepines.

DESCRIPTION OF THE RELATED ART

Certain small molecule compounds for the treatment of CRF related disorders have been disclosed in the literature (for a review see J. McCarthy et al. *Current Pharmaceutical Design* 1999, 5, 289 or P. J. Gilligan et al. *Journal of Medicinal Chemistry* 2000, 43, 1641).

McCarthy et al. (WO 96/39400) have disclosed aryl pyrimidine derivatives of the general formula

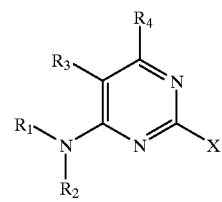

wherein X, $R_1$, $R_2$, $R_3$, and $R_4$ are defined therein, for use as CRF receptor in the treatment of central nervous system disorders. The McCarthy application only discloses arylpyrimidine compounds that contain a disubstituted amino group ($NR_1R_2$) in the 4-position of the pyrimidine ring. It is therefore surprising that the novel pyrimidinones of this invention, in which the disubstituted amino group is located on position 5 of the central heterocyclic ring, and in which the heterocycle itself presents a carbonyl group on position 4 and a substituent on the nitrogen atom on position 3, are also CRF receptor antagonists.

Murata et al. (WO 96/32383; U.S. Pat. No. 5,972,946) have disclosed the preparation of certain compounds of the general formula

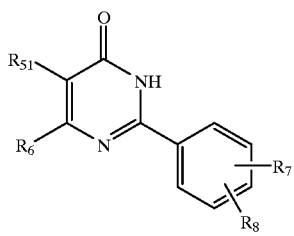

wherein $R_{51}$, $R_6$, $R_7$ and $R_8$ are defined therein, for use as synthetic intermediates in the preparation of acetamide derivatives of general formula

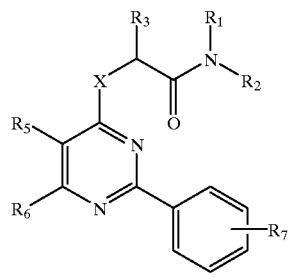

for the treatment of certain diseases.

SUMMARY OF THE INVENTION

The invention provides novel compounds of Formula I (shown below), and pharmaceutical compositions comprising compounds of Formula I and at least one pharmaceutically acceptable carrier or excipient. The invention also provides pharmaceutical manufacture, such as tablets, comprising a compound or pharmaceutically acceptable salt of Formula I. Such aryl pyrimidinone compounds bind to cell surface receptors, preferably G-coupled protein receptors, especially CRF receptors (including CRF1 and CRF2 receptors) and most preferably CRF 1 receptors. Preferred compounds of the invention exhibit high affinity for CRF receptors, preferably CRF 1 receptors. Additionally, preferred compounds of the invention also exhibit high specificity for CRF receptors (i.e., they exhibit high selectivity compared to their binding to non-CRF receptors). Preferably they exhibit high specificity for CRF 1 receptors.

Thus, the invention is directed to compounds of Formula I

Formula I

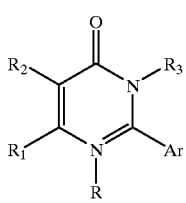

and the pharmaceutically acceptable salt thereof, wherein:
Ar is optionally substituted carbocyclic aryl or optionally substituted heteroaryl, said heteroaryl having from 1 to 3 rings, and 5 to 7 ring members in each ring and, in at least one of said rings, from 1 to about 3 heteroatoms selected from the group consisting of N, O, and S;
R is oxygen, methyl, or absent;
$R_1$ is hydrogen, halogen, cyano, hydroxy, amino, cyano, nitro, optionally substituted alkyl, optionally substituted alkenyl, optionally substituted alkynyl, optionally substituted alkoxy, optionally substituted mono- or di-alkylamino, optionally substituted cycloalkyl, optionally substituted (cycloalkyl)alkyl, optionally substituted alkylthio, optionally substituted alkylsulfinyl, optionally substituted alkylsulfonyl, or optionally substituted mono- or di-alkylcarboxamide;
$R_2$ is optionally substituted alkyl, optionally substituted alkenyl, optionally substituted alkynyl, optionally substituted alkoxy, optionally substituted mono- or di-alkylamino, optionally substituted cycloalkyl, optionally substituted (cycloalkyl)alkyl, optionally substituted heterocycloalkyl, optionally substituted alkyl ester, optionally substituted alkyl ketone, optionally substituted alkylthio, optionally substituted alkylsulfinyl, optionally substituted alkylsulfonyl, optionally substituted mono- or di-alkylcarboxamide or optionally substituted dialkylcarboxamide; and
$R_3$ is hydrogen, optionally substituted alkyl, optionally substituted alkenyl, optionally substituted alkynyl, optionally substituted alkoxy, optionally substituted mono- or di-alkylamino, optionally substituted cycloalkyl, optionally substituted (cycloalkyl)alkyl, optionally substituted alkyl ester, optionally substituted alkyl ketone, optionally substituted alkylthio, optionally substituted alkylsulfinyl, optionally substituted alkylsulfonyl, or optionally substituted mono- or di-alkylcarboxamide;
provided that $R_1$ is not hydrogen, alkyl, or trifluoromethyl when $R_2$ is hydrogen, alkyl or alkenyl.

The invention further comprises methods of treating patients suffering from certain disorders with a therapeutically effective amount of at least one compound of the invention. These disorders include CNS disorders, particularly affective disorders, anxiety disorders, stress-related disorders, eating disorders and substance abuse. The patient suffering from these disorders may be a human or other animal (preferably a mammal), such as a domesticated companion animal (pet) or a livestock animal. Preferred compounds of the invention for such therapeutic purposes are those that antagonize the binding of CRF to CRF receptors (preferably CRF1, or less preferably CRF2 receptors). The ability of compounds to act as antagonists can be measured as an $IC_{50}$ value as described below.

According to yet another aspect, the present invention provides pharmaceutical compositions comprising compounds of Formula I or the pharmaceutically acceptable salts (by which term is also encompassed pharmaceutically acceptable solvates) thereof, which compositions are useful for the treatment of the above-recited disorders. The invention further provides methods of treating patients suffering from any of the above-recited disorders with an effective amount of a compound or composition of the invention.

Additionally this invention relates to the use of the compounds of the invention (particularly labeled compounds of this invention) as probes for the localization of receptors in cells and tissues and as standards and reagents for use in determining the receptor-binding characteristics of test compounds.

Preferred arylpyrimdinone compounds of the invention exhibit good activity, i.e., a half-maximal inhibitory concentration ($IC_{50}$) of less than 1 millimolar, in the standard in vitro CRF receptor binding assay of Example 31, which follows. Particularly preferred 2,5-diarylpyrazines of the invention exhibit an $IC_{50}$ of about 1 micromolar or less, still more preferably an $IC_{50}$ of about 100 nanomolar or less even more preferably an $IC_{50}$ of about 10 nanomolar or less.

Certain particularly preferred compounds of the invention will exhibit an $IC_{50}$ of 1 nanomolar or less in such a defined standard in vitro CRF receptor binding assay.

DETAILED DESCRIPTION OF THE INVENTION

In addition to compounds of Formula I, described above, the invention is further directed to compounds and pharmaceutically acceptable salts of Formula I (shown above) wherein:

Ar is chosen from phenyl optionally substituted with up to 5 groups $R_A$, naphthyl optionally substituted with up to 5 groups $R_A$, and heteroaryl optionally substituted with up to 5 groups $R_A$, said heteroaryl having from 1 to 3 rings, 5 to 7 ring members in each ring and, in at least one of said rings, from 1 to about 3 heteroatoms selected from the group consisting of N, O, and S;

R is oxygen, methyl, or absent;

$R_1$ is chosen from hydrogen, halogen, hydroxy, cyano, nitro, haloalkyl, haloalkoxy, alkyl, alkenyl, alkynyl, alkoxy, cycloalkyl, (cycloalkyl)alkyl, mono- and di-aminoalkyl, and —S(O)$_n$alkyl;

$R_2$ is $XR_C$ or Y;

$R_3$ is chosen from hydrogen, haloalkyl, haloalkoxy, alkyl, alkenyl, alkynyl, alkoxy, cycloalkyl, (cycloalkyl)alkyl, mono- and di-aminoalkyl, and —S(O)$_n$alkyl, $XR_C$ and Y;

$R_A$ is independently selected at each occurrence from halogen, cyano, nitro, haloalkyl, haloalkoxy, hydroxy, amino, alkyl substituted with 0–2 $R_B$, alkenyl substituted with 0–2 $R_B$, alkynyl substituted with 0–2 $R_B$, cycloalkyl substituted with 0–2 $R_B$, (cycloalkyl)alkyl substituted with 0–2 $R_B$, alkoxy substituted with 0–2 $R_B$, —NH(alkyl) substituted with 0–2 $R_B$, —N(alkyl)(alkyl) of which each alkyl is independently substituted with 0–2 $R_B$, —$XR_C$, and Y;

$R_B$ is independently selected at each occurrence from the group consisting of halogen, hydroxy, cyano, amino, alkyl, —O(alkyl), —NH(alkyl), —N(alkyl)(alkyl), —S(O)$_n$(alkyl), haloalkyl, haloalkoxy, CO(alkyl), CONH(alkyl), CON(alkyl)(alkyl), —$XR_C$, and Y;

$R_C$ and $R_D$, which may be the same or different, are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, —OSiH$_2$—, —OSiH($C_1$–$C_4$alkyl)-, —OSi($C_1$–$C_4$alkyl)($C_1$–$C_4$alkyl)-, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, alkyl, —O(alkyl), —NH(alkyl), —N(alkyl)(alkyl), and —S(O)$_n$(alkyl), wherein said 3- to 7-memberered heterocyclic groups contain one or more heteroatom(s) independently selected from N, O, and S, with the point of attachment being either carbon or nitrogen; and n is independently selected at each occurrence from 0, 1, and 2;

provided that $R_1$ is not hydrogen, alkyl, or trifluoromethyl when $R_2$ is hydrogen, alkyl or alkenyl. Such compounds will be referred to as compounds of Formula IA.

Preferred compounds and salts of Formula I

Ar and R are as for Formula IA;

$R_1$ is chosen from hydrogen, halogen, hydroxy, cyano, nitro, halo($C_1$–$C_6$)alkyl, halo($C_1$–$C_6$)alkoxy, $C_1$–$C_6$alkyl, $C_2$–$C_6$alkenyl, $C_2$–$C_6$alkynyl, $C_1$–$C_6$alkoxy, $C_3$–$C_7$cycloalkyl, ($C_3$–$C_7$cycloalkyl) $C_1$–$C_4$alkyl, mono- and di-amino($C_1$–$C_6$)alkyl, and —S(O)$_n$($C_1$–$C_6$)alkyl;

$R_2$ is $XR_C$ or Y;

$R_3$ is chosen from hydrogen, halo($C_1$–$C_6$)alkyl, halo($C_1$–$C_6$) alkoxy, $C_1$–$C_6$alkyl, $C_2$–$C_6$alkenyl, $C_2$–$C_6$alkynyl, $C_1$–$C_6$alkoxy, $C_3$–$C_7$cycloalkyl, ($C_3$–$C_7$cycloalkyl) $C_1$–$C_4$alkyl, mono- and di-amino($C_1$–$C_4$)alkyl, and —S(O)$_n$($C_1$–$C_6$)alkyl, $XR_C$ and Y;

$R_A$ is independently selected at each occurrence from halogen, cyano, nitro, halo($C_1$–$C_6$)alkyl, halo($C_1$–$C_6$) alkoxy, hydroxy, amino, $C_1$–$C_6$alkyl substituted with 0–2 $R_B$, $C_2$–$C_6$alkenyl substituted with 0–2 $R_B$, $C_2$–$C_6$alkynyl substituted with 0–2 $R_B$, $C_3$–$C_7$cycloalkyl substituted with 0–2 $R_B$, ($C_3$–$C_7$cycloalkyl) $C_1$–$C_4$alkyl substituted with 0–2 $R_B$, $C_1$–$C_6$alkoxy substituted with 0–2 $R_B$, —NH($C_1$–$C_6$alkyl) substituted with 0–2 $R_B$, —N($C_1$–$C_6$alkyl)($C_1$–$C_6$alkyl) of which each $C_1$–$C_6$alkyl is independently substituted with 0–2 $R_B$, —$XR_C$, and Y;

$R_B$ is independently selected at each occurrence from the group consisting of:

i) halogen, hydroxy, cyano, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), —S(O)$_n$(alkyl), halo($C_1$–$C_4$)alkyl, halo($C_1$–$C_4$)alkoxy, CO($C_1$–$C_4$alkyl), CONH($C_1$–$C_4$alkyl), CON($C_1$–$C_4$alkyl)($C_1$–$C_4$alkyl), —$XR_C$, and ii) morpholino, pyrrolidino, piperidino, thiomorpholino, and piperazino, each of which is optionally substituted with up to three substituents independently chosen from hydroxy, halogen, alkyl and alkoxy;

$R_C$ and $R_D$, which may be the same or different, are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)

$_n$NH—, —S(O)$_n$NR$_D$—, —OC(=S)S—, —NHC(=O)—, —NR$_D$C(=O)—, —NHS(O)$_n$—, —OSiH$_2$—, OSiH(C$_1$–C$_4$alkyl)-, —OSi(C$_1$–C$_4$alkyl)(C$_1$–C$_4$alkyl)-, and —NR$_D$S(O)$_n$—;

Y and Z are independently selected at each occurrence from:
3- to 7-membered carbocyclic or heterocyclic groups which are saturated, unsaturated, or aromatic, which may be further substituted with one or more substituents independently selected from halogen, oxo, hydroxy, amino, cyano, C$_1$–C$_4$alkyl, —O(C$_1$–C$_4$alkyl), —NH(C$_1$–C$_4$alkyl), —N(C$_1$–C$_4$alkyl)(C$_1$–C$_4$alkyl), and —S(O)$_n$(alkyl), wherein said 3- to 7-memberered heterocyclic groups contain one or more heteroatom(s) independently selected from N, O, and S, with the point of attachment being either carbon or nitrogen; and n is independently selected at each occurrence from 0, 1, and 2;

provided that R$_1$ is not hydrogen, alkyl, or trifluoromethyl when R$_2$ is hydrogen, alkyl or alkenyl, provided that R$_1$ is not hydrogen, alkyl, or trifluoromethyl when R$_2$ is hydrogen, alkyl or alkenyl. Such compounds will be referred to as compounds of Formula IB.

Also provided by the invention are compounds and salts of Formula IA and IB, wherein R is absent;

Ar is chosen from phenyl, naphthyl, pyridyl, pyrimidinyl, pyrazinyl, pyridizinyl, thienyl, thiazolyl, oxazolyl, isoxazolyl, pyrrolyl, furanyl, and triazolyl, each of which is optionally substituted with up to 5 independently chosen groups R$_A$, wherein at least one position of said phenyl that is ortho or para to the point of attachment of Ar in Formula I is substituted.

More preferably Ar is chosen from phenyl, naphthyl, or pyridyl each of which is substituted with from 1 to 5 independently chosen groups R$_A$, wherein at least one position of Ar that is ortho or para to the point of attachment of Ar in Formula I is substituted.

Most preferably Ar is phenyl which is substituted with from 1 to 5 independently chosen groups R$_A$, wherein at least one position of Ar that is ortho or para to the point of attachment of Ar in Formula I is substituted.

Other preferred compounds and salts of Formula IA and Formula IB are those wherein:

R is absent;

Ar is phenyl substituted with from 1 to 5 independently chosen groups R$_A$, wherein at least one position of Ar that is ortho or para to the point of attachment of Ar in Formula I is substituted;

R$_1$ is selected from hydrogen, halogen, C$_1$–C$_4$alkyl, C$_1$–C$_4$alkoxy, halo(C$_1$–C$_2$)alkyl, and halo(C$_1$–C$_2$)alkoxy; and R$_3$ is selected from hydrogen, halogen, C$_1$–C$_6$alkyl, C$_1$–C$_6$alkoxy, halo(C$_1$–C$_4$)alkyl, halo(C$_1$–C$_4$)alkoxy, (C$_3$–C$_7$cycloalkyl)C$_1$–C$_4$alkyl, pyrrolidin-1-yl(C$_1$–C$_4$)alkyl, piperidin-1-yl(C$_1$–C$_4$)alkyl, piperazin-1-yl(C$_1$–C$_4$)alkyl, morpholin-4-yl(C$_1$–C$_4$)alkyl, and thiomorpholin-4-yl(C$_1$–C$_4$)alkyl.

Also included in the invention are compounds and salts of Formula IA and IB wherein R is absent;

Ar is phenyl substituted with from 1 to 5 independently chosen groups R$_A$, wherein at least one position of Ar that is ortho or para to the point of attachment of Ar in Formula I is substituted; and R$_C$ and R$_D$, which may be the same or different, are independently selected at each occurrence from:

hydrogen, and straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds.

Further provided by the invention are compounds and salts of Formula IA and Formula IB wherein:

R is absent;

Ar is phenyl substituted with from 1 to 5 independently chosen groups R$_A$, wherein at least one position of Ar that is ortho or para to the point of attachment of Ar in Formula I is substituted;

R$_1$ is selected from hydrogen, halogen, C$_1$–C$_4$alkyl, C$_1$–C$_4$alkoxy, halo(C$_1$–C$_2$)alkyl, and halo(C$_1$–C$_2$)alkoxy;

R$_3$ is selected from hydrogen, halogen, C$_1$–C$_6$alkyl, C$_1$–C$_6$alkoxy, halo(C$_1$–C$_4$)alkyl, halo(C$_1$–C$_4$)alkoxy, (C$_3$–C$_7$cycloalkyl)C$_1$–C$_4$alkyl, pyrrolidino-1-yl(C$_1$–C$_4$)alkyl, piperidin-1-yl(C$_1$–C$_4$)alkyl, piperazin-1-yl(C$_1$–C$_4$)alkyl, morpholin-4-yl(C$_1$–C$_4$)alkyl, and thiomorpholin-4-yl(C$_1$–C$_4$)alkyl; and R$_C$ and R$_D$, which may be the same or different, are independently selected at each occurrence from:

hydrogen, and straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds.

Other preferred R$_2$ groups for compounds of Formula IA and Formula IB are groups of the formula

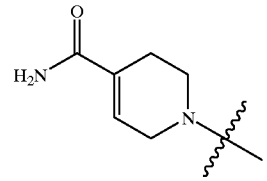

and groups of the formula

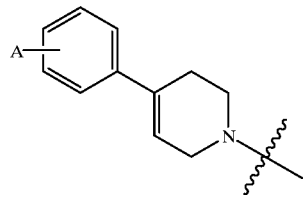

where A represents up to three groups independently chosen from hydrogen, halogen, alkyl, and alkoxy.

The invention further provides compounds and salts of Formula II, Formula III, Formula IV wherein Formula II

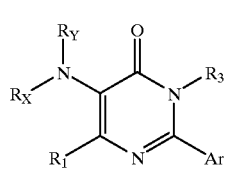

-continued

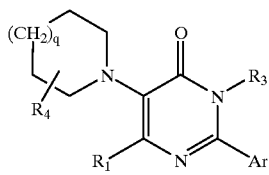

Formula III

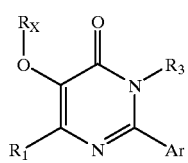

Formula IV wherein:
$R_X$ and $R_Y$ are independently chosen from hydrogen, $C_1$–$C_6$alkyl$_1$, $(C_3$–$C_7$cycloalkyl$_2)C_1$–$C_4$alkyl$_1$, and mono- and di($C_1$–$C_6$)alkyl$_1$amino;
where each alkyl$_1$ is independently straight, branched, or cyclic, contains zero or 1 or more double or triple bonds, and is optionally substituted with one or more substituents independently chosen from halogen, hydroxy, amino, oxo, cyano, $C_1$–$C_4$alkoxy, and mono- and di($C_1$–$C_4$)alkylamino,
where each $C_3$–$C_7$cycloalkyl$_2$ is optionally substituted by one or more substituents independently chosen from halogen, amino, hydroxy, oxo, cyano, $C_1$–$C_4$alkoxy, and mono- or di($C_1$–$C_4$)alkylamino;
$R_1$, $R_3$ and Ar are as defined Formula IA or Formula IB;
and for Formula IV,
$R_4$ represents up to three substituents independently chosen from hydrogen, halogen, $C_1$–$C_6$alkyl, and $C_1$–$C_6$ alkoxy; and
q is 0, 1, or 2.

More preferred compounds and salts of Formula II, Formula III, and Formula IV are those wherein
Ar is phenyl, naphthyl, pyridyl, pyrimidinyl, pyrazinyl, pyridizinyl, thienyl, thiazolyl, oxazolyl, isoxazolyl, pyrrolyl, furanyl, and triazolyl, each of which is optionally substituted with up to 5 independently chosen groups $R_A$, where $R_A$ is as defined for Formula IA or more preferably as defined for compounds of Formula IB and wherein at least one position of said phenyl that is ortho or para to the point of attachment of Ar in Formula IA or IB is substituted.
More preferably Ar is chosen from phenyl, naphthyl, and pyridyl (where phenyl is particularly preferred), each of which is substituted with from 1 to 5 independently chosen groups $R_A$, wherein at least one position of Ar that is ortho or para to the point of attachment of Ar in Formula II, Formula III, or Formula IV is substituted; and for Formula IV,
$R_4$ represents up to three substituents independently chosen from hydrogen, halogen, $C_1$–$C_6$alkyl, and $C_1$–$C_6$ alkoxy; and
q is 0, 1, or 2.

Other preferred compounds and salts of Formula II, Formula III and Formula IV include those wherein:
Ar is phenyl substituted with from 1 to 5 independently chosen groups $R_A$, wherein at least one position of Ar that is ortho or para to the point of attachment of Ar in Formula II, Formula III and Formula IV is substituted;
$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy;

$R_3$ is selected from hydrogen, $C_1$–$C_6$alkyl, $C_1$–$C_6$alkoxy, halo($C_1$–$C_4$)alkyl, halo($C_1$–$C_4$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl;
and for Formula IV,
$R_4$ represents up to three substituents independently chosen from hydrogen, halogen, $C_1$–$C_6$alkyl, and $C_1$–$C_6$ alkoxy; and
q is 0, 1, or 2.

Additional embodiments of the invention include compounds and salts of Formula II, Formula II, and Formula IV, wherein
Ar is phenyl substituted with from 1 to 5 independently chosen groups $R_A$, wherein at least one position of Ar that is ortho or para to the point of attachment of Ar in Formula II, Formula III and Formula IV is substituted;
$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy; and
$R_3$ is selected from hydrogen, $C_1$–$C_6$alkyl, $C_1$–$C_6$alkoxy, halo($C_1$–$C_4$)alkyl, halo($C_1$–$C_4$)alkoxy, ($C_3$–$C_7$cycloalkyl)$C_1$–$C_4$alkyl, pyrrolidino-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl;
and
$R_C$ and $R_D$, which may be the same or different, are independently selected at each occurrence from:
hydrogen, and straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds;
and for Formula IV,
$R_4$ represents up to three substituents independently chosen from hydrogen, halogen, $C_1$–$C_6$alkyl, and $C_1$–$C_6$ alkoxy; and
q is 0, 1, or 2.

The invention is particularly directed to compounds and salts of Formula II, Formula III and Formula IV wherein
Ar is phenyl substituted with from 1 to 3 substituents independently chosen from:
halogen, cyano, nitro, halo($C_1$–$C_4$)alkyl, halo($C_1$–$C_4$)alkoxy, hydroxy, amino, $C_3$–$C_7$ cycloalkyl, ($C_3$–$C_7$cycloalkyl) ($C_1$–$C_4$)alkyl, $C_1$–$C_6$alkyl substituted with 0–2 $R_B$, $C_1$–$C_6$alkoxy substituted with 0–2 $R_B$, —NH($C_1$–$C_4$alkyl) substituted with 0–2 $R_B$, —N($C_1$–$C_4$alkyl)($C_1$–$C_4$alkyl) of which each $C_1$–$C_4$alkyl is independently substituted with 0–2 $R_B$,
wherein at least one position of Ar that is ortho or para to the point of attachment of Ar in Formula II, Formula III and Formula IV is substituted;
$R_B$ is independently selected at each occurrence from the group consisting of:
i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and
ii) morpholino, pyrrolidino, piperidino, thiomorpholino, and piperazino;
$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy;
$R_3$ is selected from hydrogen, $C_1$–$C_6$alkyl, $C_1$–$C_6$alkoxy, halo($C_1$–$C_4$)alkyl,
halo($C_1$–$C_4$)alkoxy, ($C_3$–$C_7$cycloalkyl)$C_1$–$C_4$alkyl, pyrrolidin-1-yl($C_1$–$C_4$)alkyl,
piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl ($C_1$–$C_4$)alkyl;
and for Formula IV, $R_4$ represents up to three substituents independently chosen from hydrogen, halogen, $C_1$–$C_6$alkyl, and $C_1$–$C_6$ alkoxy; and q is 0, 1, or 2.

Particularly preferred compounds and salts of Formula II, Formula III, and Formula IV are those wherein:

Ar is phenyl substituted with from 1 to 3 substituents independently chosen from:

halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl)$C_1$–$C_4$alkyl, mono and di($C_1$–$C_4$)alkylamino, $C_1$–$C_6$alkyl substituted with 0–2 $R_B$, $C_1$–$C_6$alkoxy substituted with 0–2 $R_B$, wherein at least one position of Ar that is ortho or para to the point of attachment of Ar in Formula II, Formula III and Formula IV is substituted;

$R_B$ is independently selected at each occurrence from the group consisting of:

i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$)alkoxy; and $R_3$ is selected from hydrogen, $C_1$–$C_4$alkyl, $C_1$–$C_4$alkoxy, halo($C_1$–$C_2$)alkyl, halo($C_1$–$C_2$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl;

and for Formula IV, $R_4$ represents up to three substituents independently chosen from hydrogen, halogen, $C_1$–$C_6$alkyl, and $C_1$–$C_6$ alkoxy; and q is 0, 1 or 2.

Additionally, the invention provides compounds of Formula II and Formula III wherein $R_X$ and $R_Y$ are the same or different and are independently selected from hydrogen or straight, branched or cyclic alkyl groups, optionally containing one or more aza or oxa bridge, and optionally containing one or more double or triple bonds; and $R_1$, $R_3$ and Ar are as defined Formula IA or Formula IB.

Further provided by the invention are compounds and salts of Formula V–Formula IX Formula V

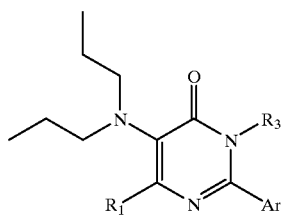

Formula VI

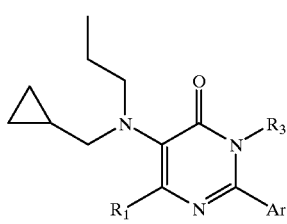

Formula VII

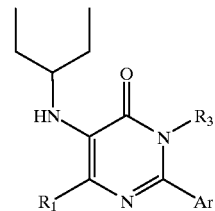

Formula VIII

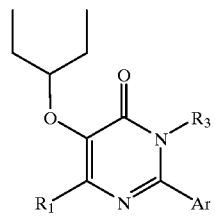

Formula IX

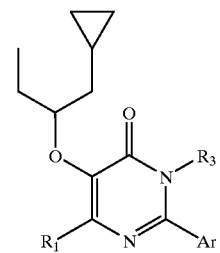

wherein

Ar is phenyl substituted with from 1 to 3 substituents independently chosen from:

halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl)$C_1$–$C_4$alkyl, mono and di($C_1$–$C_4$)alkylamino, $C_1$–$C_6$alkyl substituted with 0–2 $R_B$, $C_1$–$C_6$alkoxy substituted with 0–2 $R_B$, wherein at least one position of Ar that is ortho or para to the point of attachment of Ar in Formula V–Formula IX is substituted;

$R_B$ is independently selected at each occurrence from the group consisting of:

i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$)alkoxy; and $R_3$ is selected from hydrogen, $C_1$–$C_4$alkyl, $C_1$–$C_4$alkoxy, halo($C_1$–$C_2$)alkyl, halo($C_1$–$C_2$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl.

Compounds of the invention are useful in treating a variety of conditions including affective disorders, anxiety disorders, stress disorders, eating disorders, and drug addiction.

Affective disorders include all types of depression, bipolar disorder, cyclothymia, and dysthymia.

Anxiety disorders include generalized anxiety disorder, panic, phobias and obsessive-compulsive disorder.

Stress-related disorders include post-traumatic stress disorder, hemorrhagic stress, stress-induced psychotic episodes, psychosocial dwarfism, stress headaches, stress-induced immune systems disorders such as stress-induced fever, and stress-related sleep disorders.

Eating disorders include anorexia nervosa, bulimia nervosa, and obesity.

Modulators of the CRF receptors are also useful in the treatment (e.g., symptomatic treatment)of a variety of neurological disorders including supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, disorders of pain perception such as fibromyalgia and epilepsy.

Additionally compounds of Formula I are useful as modulators of the CRF receptor in the treatment (e.g., symptomatic treatment) of a number of gastrointestinal, cardiovascular, hormonal, autoimmune and inflammatory conditions. Such conditions include irritable bowel syndrome, ulcers, Crohn's disease, spastic colon, diarrhea, post operative ilius and colonic hypersensitivity associated with psychopathological disturbances or stress, hypertension, tachycardia, congestive heart failure, infertility, euthyroid sick syndrome, inflammatory conditions effected by rheumatoid arthritis and osteoarthritis, pain, asthma, psoriasis and allergies.

Compounds of Formula I are also useful as modulators of the CRF1 receptor in the treatment of animal disorders associated with aberrant CRF levels. These conditions include porcine stress syndrome, bovine shipping fever, equine paroxysmal fibrillation, and dysfunctions induced by confinement in chickens, sheering stress in sheep or human-animal interaction related stress in dogs, psychosocial dwarfism and hypoglycemia.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and other domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids (e.g., blood, plasma, serum, CSF, lymph, cellular interstitial fluid, aqueous humor, saliva, synovial fluid, feces, or urine) and cell and tissue samples of the above subjects will be suitable for use.

The CRF binding compounds provided by this invention and labeled derivatives thereof are also useful as standards and reagents in determining the ability of test compounds (e.g., a potential pharmaceutical) to bind to a CRF receptor.

Labeled derivatives the CRF antagonist compounds provided by this invention are also useful as radiotracers for positron emission tomography (PET) imaging or for single photon emission computerized tomography (SPECT).

More particularly compounds of the invention may be used for demonstrating the presence of CRF receptors in cell or tissue samples. This may be done by preparing a plurality of matched cell or tissue samples, at least one of which is prepared as an experiment sample and at least one of which is prepared as a control sample. The experimental sample is prepared by contacting (under conditions that permit binding of CRF to CRF receptors within cell and tissue samples) at least one of the matched cell or tissue samples that has not previously been contacted with any compound or salt of the invention with an experimental solution comprising the detectably-labeled preparation of the selected compound or salt at a first measured molar concentration. The control sample is prepared by in the same manner as the experimental sample and is incubated in a solution that contains the same ingredients as the experimental solution but that also contains an unlabelled preparation of the same compound or salt of the invention at a molar concentration that is greater than the first measured molar concentration.

The experimental and control samples are then washed to remove unbound detectably-labeled compound. The amount of detectably-labeled compound remaining bound to each sample is then measured and the amount of detectably-labeled compound in the experimental and control samples is compared. A comparison that indicates the detection of a greater amount of detectable label in the at least one washed experimental sample than is detected in any of the at least one washed control samples demonstrates the presence of CRF receptors in that experimental sample.

The detectably-labeled compound used in this procedure may be labeled with any detectable label, such as a radioactive label, a biological tag such as biotin (which can be detected by binding to detectably-labeled avidin), an enzyme (e.g., alkaline phosphatase, beta galactosidase, or a like enzyme that can be detected its activity in a colorimetric assay) or a directly or indirectly luminescent label. When tissue sections are used in this procedure and the detectably-labeled compound is radiolabeled, the bound, labeled compound may be detected autoradiographically to generate an autoradiogram. When autoradiography is used, the amount of detectable label in an experimental or control sample may be measured by viewing the autoradiograms and comparing the exposure density of the autoradiograms.

The present invention also pertains to methods of inhibiting the binding of CRF to CRF receptors (preferably CFR1 receptors) which methods involve contacting a solution containing a CRF antagonist compound of the invention with cells expressing CRF receptors, wherein the compound is present in the solution at a concentration sufficient to inhibit CRF binding to CRF receptors in vitro. This method includes inhibiting the binding of CRF to CRF receptors in vivo, e.g., in a patient given an amount of a compound of Formula I that would be sufficient to inhibit the binding of CRF to CRF receptors in vitro. In one embodiment, these methods are useful in treating physiological disorders associated with excess concentrations of CRF. The amount of a compound that would be sufficient to inhibit the binding of a CRF to the CRF receptor may be readily determined via a CRF receptor binding assay (see, e.g., Example 31), or from the $EC_{50}$ of a CRF receptor functional assay, such as a standard assay of CRF receptor mediated chemotaxis. The CRF receptors used to determine in vitro binding may be obtained from a variety of sources, for example from cells that naturally express CRF receptors, e.g. IMR32 cells or from cells expressing cloned human CRF receptors.

The present invention also pertains to methods for altering the activity of CRF receptors, said method comprising exposing cells expressing such receptors to an effective amount of a compound of the invention, wherein the compound is present in the solution at a concentration sufficient to specifically alter the signal transduction activity in response to CRF in cells expressing CRF receptors in vitro, preferred cells for this purpose are those that express high levels of CRF receptors (i.e., equal to or greater than the number of CRF1 receptors per cell found in differentiated IMR-32 human neuroblastoma cells), with IMR-32 cells being particularly preferred for testing the concentration of a compound required to alter the activity of CRF1 receptors. This method includes altering the signal transduction activity of CRF receptors in vivo, e.g., in a patient given an amount of a compound of Formula I that would be sufficient to alter the signal transduction activity in response to CRF in cells expressing CRF receptors in vitro. The amount of a compound that would be sufficient to alter the signal transduction activity in response to CRF of CRF receptors may also be determined via an assay of CRF receptor mediated signal transduction, such as an assay wherein the binding of CRF to a cell surface CRF receptor effects a changes in reporter gene expression.

The present invention also pertains to packaged pharmaceutical compositions for treating disorders responsive to CRF receptor modulation, e.g., eating disorders, depression or stress. The packaged pharmaceutical compositions include a container holding a therapeutically effective amount of at least one CRF1 receptor modulator as described supra and instructions for using the treating disorder responsive to CRF1 receptor modulation in the patient.

Chemical Description and Terminology

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

Formula I includes, but is not limited to, compounds of Formula IA, Formula IB, and Formula II–Formula IX.

As indicated above, various substituents of the various formulae (compounds of Formula I, IA, IB, II, etc.) are "optionally substituted", including arylpyrimidinone compounds of Formula I and subformulae thereof, and such substituents as recited in the sub-formulae such as Formula I and subformulae. The term "substituted," as used herein, means that any one or more hydrogens on the designated atom or group is replaced with a selection from the indicated group of substituents, provided that the designated atom's normal valence is not exceeded, and that the substitution results in a stable compound. When a substituent is oxo (keto, i.e., =O), then 2 hydrogens on an atom are replaced. The present invention is intended to include all isotopes (including radioisotopes) of atoms occurring in the present compounds.

When substituents such as Ar, $R_1$, $R_2$, and $R_3$ are further substituted, they may be so substituted at one or more available positions, typically 1 to 3 or 4 positions, by one or more suitable groups such as those disclosed herein. Suitable groups that may be present on a "substituted" Ar, $R_1$, $R_2$, and $R_3$ or other group include e.g., halogen; cyano; hydroxyl; nitro; azido; alkanoyl (such as a $C_1$–$C_6$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; carbocyclic aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

As used herein, the term "aryl" includes groups that contain 1 to 3 separate or fused rings and from 6 to about 18 ring atoms, without hetero atoms as ring members. Specifically preferred carbocyclic aryl groups include phenyl, and naphthyl including 1-napthyl and 2-naphthyl.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_1$–$C_{10}$ alkyl groups. Especially preferred alkyl groups are methyl, ethyl, propyl, butyl, and 3-pentyl. The term $C_{1-4}$ alkyl as used herein includes alkyl groups consisting of 1 to 4 carbon atoms, which may contain a cyclopropyl moiety. Suitable examples are methyl, ethyl, and cyclopropylmethyl.

"Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_3$–$C_7$cycloalkyl)$C_1$–$C_4$alkyl", cycloalkyl, and alkyl are as defined above, and the point of attachment is on the alkyl group. This term encompasses, but is not limited to, cyclopropylmethyl, cyclohexylmethyl, and cyclohexylmethyl.

"Alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 8 carbon atoms, more typically 2 to about 6 carbon atoms.

"Alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 8 carbon atoms, more typically 2 to about 6 carbon atoms.

"Haloalkyl" is intended to include both branched and straight-chain saturated aliphatic hydrocarbon groups having the specified number of carbon atoms, substituted with 1 or more halogen atoms. Preferred examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups will have 1 to about 8 carbon atoms, more typically 1 to about 6 carbon atoms.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 8 carbon atoms, more typically 1 to about 6 carbon atoms.

"Halolkoxy" represents a haloalkyl group as defined above with the indicated number of carbon atoms attached through an oxygen bridge. Preferred examples of haloalkoxy groups include trifluoromethoxy, 2-fluoroethoxy, and difluromethoxy.

As used herein, the term "alkylthio" includes those groups having one or more thioether linkages and preferably from 1 to about 8 carbon atoms, more typically 1 to about 6 carbon atoms.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl (SO$_2$) linkage groups and typically from 1 to about 8 carbon atoms, more typically 1 to about 6 carbon atoms.

As used herein, the term "alkylamino" includes those groups having one or more primary, secondary and/or tertiary amine groups and typically from 1 to about 8 carbon atoms, more typically 1 to about 6 carbon atoms.

"Halo" or "halogen" as used herein refers to fluoro, chloro, bromo, or iodo; and "counter-ion" is used to represent a small, negatively charged species such as chloride, bromide, hydroxide, acetate, sulfate, and the like.

As used herein, "carbocyclic group" is intended to mean any stable 3- to 7-membered monocyclic or bicyclic or 7-to 13-membered bicyclic or tricyclic group, any of which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, adamantyl, cyclooctyl, [3.3.0]bicyclooctanyl, [4.3.0] bicyclononanyl, [4.4.0]bicyclodecanyl, [2.2.2] bicyclooctanyl, fluorenyl, phenyl, naphthyl, indanyl, and tetrahydronaphthyl.

As used herein, the term "heterocyclic group" is intended to include saturated, partially unsaturated, or unsaturated (aromatic) groups having 1 to 3 (preferably fused) rings with 3 to about 8 members per ring at least one ring containing an atom selected from N, O or S. The nitrogen and sulfur heteroatoms may optionally be oxidized. The term or "heterocycloalkyl" is used to refer to saturated heterocyclic groups.

The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. As used herein, the term "aromatic heterocyclic system" is intended to include any stable 5-to 7-membered monocyclic or 10- to 14-membered bicyclic heterocyclic aromatic ring system which comprises carbon atoms and from 1 to 4 heteroatoms independently selected from the group consisting of N, O and S. It is preferred that the total number of S and O atoms in the aromatic heterocycle is not more than 2, more preferably not more than 1.

Examples of heterocycles include, but are not limited to, those exemplified elsewhere herein and further include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;- 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl.

Preferred heterocyclic groups include, but are not limited to, pyridinyl, pyrimidinyl, furanyl, thienyl, pyrrolyl, pyrazolyl, pyrrolidinyl, morpholinyl, thiomorpholinyl, piperidinyl, piperazinyl, and imidazolyl. Also included are fused ring and spiro compounds containing, for example, the above heterocycles.

As used herein, "pharmaceutically acceptable salts" refer to derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)$n-COOH where n is 0–4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

"Prodrugs" are intended to include any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. The term "therapeutically effective amount" of a compound of this invention means an amount effective, when administered to a human or non-human patient, to provide a therapeutic benefit such as an amelioration of symptoms, e.g., an amount effective to antagonize the effects of pathogenic levels of CRF or to treat the symptoms of stress disorders, affective disorder, anxiety or depression.

Pharmaceutical Preparations

The compounds of general Formula I may be administered orally, topically, transdermally, parenterally, by inhalation or spray or rectally or vaginally in dosage unit formulations containing conventional non-toxic pharmaceutically acceptable carriers, adjuvants and vehicles. The term parenteral as used herein includes subcutaneous, intravenous, intramuscular, intrathecal and like types of injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at body temperature and will therefore melt in the body to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, one or more adjuvants such as preservatives, buffering agents, or local anesthetics can also be present in the vehicle.

Dosage levels of the order of from about 0.05 mg to about 100 mg per kilogram of body weight per day are useful in the treatment of the above-indicated conditions, preferred dosages range from about 0.1 to about 30 mg per kg and more preferably from about 0.5 to about 5 mg per kg per subject per day. The amount of active ingredient that may be combined with the carrier materials to produce a single dosage form will vary depending upon the host treated and the particular mode of administration. Dosage unit forms will generally contain between from about 0.1 mg to about 750 mg of an active ingredient.

Frequency of dosage may also vary depending on the compound used and the particular disease treated. However, for treatment of most CNS and gastrointestinal disorders, a dosage regimen of four times daily, preferably three times daily, more preferably two times daily and most preferably once daily is contemplated. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

Preferred compounds of the invention will have certain pharmacological properties. Such properties include, but are not limited to oral bioavailability, such that the preferred oral dosage forms discussed above can provide therapeutically effective levels of the compound in vivo. Penetration of the blood brain barrier is necessary for most compounds used to treat CNS disorders, while low brain levels of compounds used to treat periphereal disorders are generally preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity, with non-toxic compounds being preferred. Penetration of the blood brain barrier of a compound in humans may be predicted from the brain levels of the compound in laboratory animals given the compound, e.g., intravenously.

Percentage of serum protein binding may be predicted from albumin binding assays. Examples of such assays are described in a review by Oravcová, et al. (Journal of Chromatography B (1996) volume 677, pages 1–27). Preferred compounds exhibit reversible serum protein binding. Preferably this binding is less than 99%, more preferably less than 95%, even more preferably less than 90%, and most preferably less than 80%.

Frequency of administration is generally inversely proportional to the in vivo half-life of a compound. In vivo half-lives of compounds may be predicted from in vitro assays of microsomal half-life as described by Kuhnz and Gieschen (Drug Metabolism and Disposition, (1998) volume 26, pages 1120–1127). Preferred half lives are those allowing for a preferred frequency of administration.

As discussed above, preferred compounds of the invention exhibit good activity in standard in vitro CRF receptor binding assays, preferably the assay as specified in Example 31, which follows. References herein to "standard in vitro receptor binding assay" are intended to refer to that protocol as defined in Example 31, which follows. Generally preferred compounds of the invention have an $IC_{50}$ (half-maximal inhibitory concentration) of about 1 micromolar or less, still more preferably and $IC_{50}$ of about 100 nanomolar or less even more preferably an $IC_{50}$ of about 10 nanomolar or less or even 1 nanomolar or less in such a defined standard in vitro CRF receptor binding assay as exemplified by Example 31 which follows.

EXAMPLES

Preparation of Arylpyrimidinones

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. Preferred methods for the preparation of compounds of the present invention include, but are not limited to, those described in Schemes I, II and III. Those who are skilled in the art will recognize that the starting materials may be varied and additional steps employed to produce compounds encompassed by the present invention. All references cited herein are hereby incorporated in their entirety herein by reference. The following abbreviations are used herein:

| | | | |
|---|---|---|---|
| AcOH | acetic acid | DMF | N,N-dimethylformamide |
| DMSO | Dimethylsulfoxide | $Et_2O$ | diethyl ether |
| EtOAc | ethyl acetate | EtOH | Ethanol |
| LDA | lithium diisopropylamide | NaH | sodium hydride |
| NaHMDS | sodium hexamethyldisilazane | HCl | hydrochloric acid |
| THF | tetrahydrofuran | | |
| EX# | example number | | |

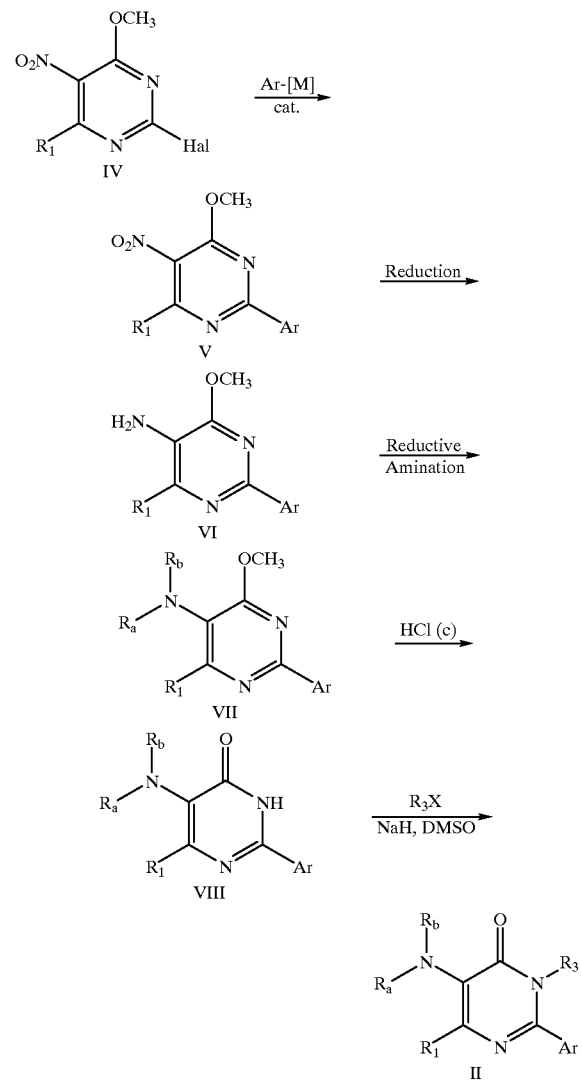

dure (T. L. Cupps et al., *Journal of Organic Chemistry* 1983, 48, 1060). The halopyrimidine IV can be converted to arylpyrimidine V by a transition metal-catalyzed coupling reaction with a metalloaryl reagent (Ar-[M]). More commonly employed reagent/catalyst pairs include aryl boronic acid/palladium(0) (Suzuki reaction; N. Miyaura and A. Suzuki, *Chemical Reviews* 1995, 95, 2457), aryl trialkylstannane/palladium(0) (Stille reaction; T. N. Mitchell, *Synthesis* 1992, 803), arylzinc/palladium(0) and aryl Grignard/nickel(II). Palladium(0) represents a catalytic system made of a various combination of metal/ligand pair which includes, but not limited to, tetrakis (triphenylphosphine)-palladium(0), palladium(II) acetate/tri (o-tolyl)phosphine, tris-(dibenzylideneacetone) dipalladium (0)/tri-tert-butyl-phosphine and dichloro[1,1'-bis (diphenylphosphine)-ferrocene]palladium(0). Nickel(II) represents a nickel-containing catalyst such as [1,2-bis(diphenyl-phosphino)ethane]dichloronickel(II) and [1,3-bis (diphenyl-phosphino)propane]dichloronickel(II). Reduction of the nitro group in V may be accomplished by a variety of methods known in the art, including hydrogenation with hydrogen and transition metal catalysts or the use of sodium hydrosulfite in aqueous solutions to give VI. The amino pyrimidine VI may be transformed into VII by reductive amination using aldehydes and reducing agents such as sodium triacetoxyborohydride in inert solvents. Depending on the substitution on the aromatic group (Ar), the order of the steps in Scheme I may be altered. For instance, for disubstituted aromatic analogs, compound IV may first be coupled with a boronic acid, the nitro group reduced and the resulting amine alkylated to give compounds of generic structure VII. Conversion of the methoxypyrimidine VII to the pyrimidinone VIII may be carried out by a number of methods known in the art, including for example the use of hydrochloric acid, boron trichloride, boron tribromide, acetic acid, trimethylsilyl bromide, trimethylsilyl chloride, or aluminum tribromide, in a solvent such as dichloromethane or DMF.

N-alkylation of pyrimidone VIII to the final target II may be accomplished using a base such as but not limited to alkali metal hydride or alkali metal alkoxide in inert solvents such as but not limited to THF, DMF, or methyl sulfoxide. Alkylation may be conducted using alkyl halide, suitably bromide, iodide, tosylate or mesylate at temperatures ranging from −78° C. to 100° C.

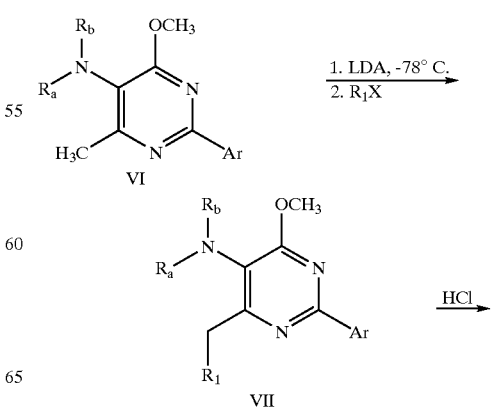

According to the general method A, wherein $R_1$ and $R_3$ are as defined for formula I and Hal represents a halogen atom, suitably chloride or bromide. Compounds of formula IV can be prepared according to a known literature proce-

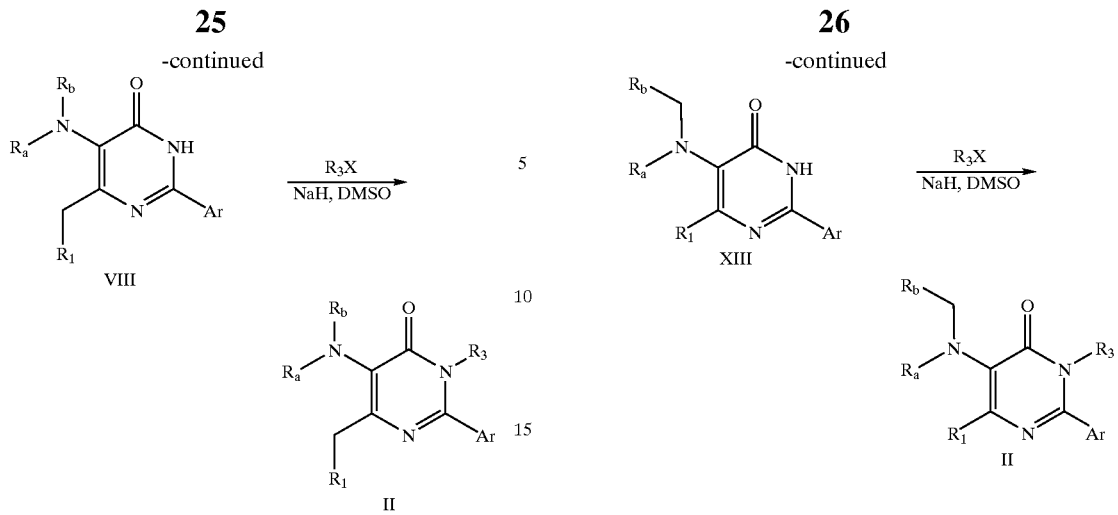

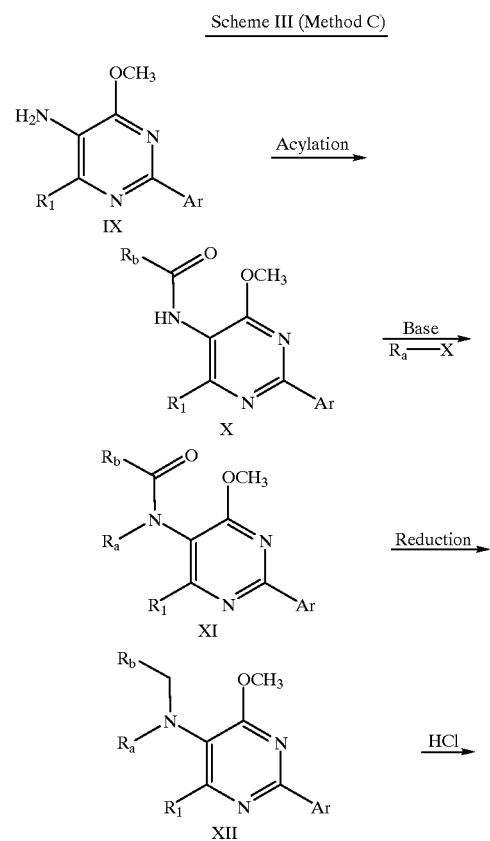

The alkylation of the methyl group (or other alkyl group) on position 6 of the pyrimidine (e.g. compound VI) may be accomplished using a strong base such as but not limited to alkali metal hydride, alkali metal amide, or alkali metal alkoxide in inert solvents such as but not limited to THF, DMF, or methyl sulfoxide. Alkylation may be conducted using alkyl halide, suitably bromide, iodide, tosylate or mesylate at temperatures ranging from −78° C. to 100° C. Using the same methods described in Method A, compounds of the formula II can also be prepared as outlined in Scheme II An alternative method for introducing the substituents $R_A$ and $R_B$ to give compounds of the formula II is outlined in Scheme III and may be accomplished by a variety of methods known in the art. These include reaction of the amine IX with acid chlorides or anhydrides in the presence of bases such as but not limited to triethylamine or pyridine in inert solvents such as dichloromethane or toluene. The N—H group is then deprotonated by a strong base such as but not limited to alkali metal hydride, alkali metal amide, or alkali metal alkoxide in inert solvents such as but not limited to THF, DMF, or methyl sulfoxide. Alkylation may be conducted using alkyl halide, suitably bromide or iodide, at temperatures ranging from 0° C. to 100° C. Reduction of the amide XI with reducing agents such as but not limited to lithium aluminum hydride, borane or diiso-butylaluminum hydride in inert solvents such as but not limited to THF, ether, or toluene furnishes compounds of the formula XII. Using the same methods described in Method A, compounds of the formula II can also be prepared as outlined in Scheme III.

The preparation of the compounds of the present invention is illustrated further by the following examples, which are not to be construed as limiting the invention in scope or spirit to the specific procedures and compounds described in them.

Commercial reagents are used without further purification. Room or ambient temperature refers to 20 to 25° C. Concentration in vacuo implies the use of a rotary evaporator. TLC refers to thin layer chromatography. Proton nuclear magnetic resonance ($^1$H NMR) spectral data are obtained at 300 or 400 MHz. Mass spectral data are obtained either by CI or APCI methods.

Example 1

5-Dipropylamino-2-(2-methoxy-4,6-dimethyl-phenyl)-3,6-dimethyl-3H-pyrimidin-4-one [Formula I: Ar=2-methoxy-4,6-dimethyl-phenyl; $R_2$=N(CH$_2$CH$_2$CH$_3$)$_2$; $R_3$=CH$_3$]

A: 4-Methoxy-2-(2-methoxy-4,6-dimethyl-phenyl)-6-methyl-5-nitro-pyrimidine. A solution of 2-chloro-4-methoxy-6-methyl-5-nitro-pyrimidine (2.03 g, 10 mmol) and tetrakis(tri-phenylphosphine)palladium(0) (225 mg) in ethyleneglycol dimethyl ether (50 mL) is stirred at room temperature for 15 min, then 2-methoxy-4,6-dimethyl-benzeneboronic acid (3.60 g, 20 mmol) and an aqueous solution of sodium carbonate (1.0 M, 10 mL) is added sequentially. The mixture is stirred at 75° C. (oil bath temperature) for 1.5 h, then diluted with 0.1 N sodium hydroxide and extracted twice with 1:1 hexane-ethyl ether. Combined extracts are dried (magnesium sulfate), filtered, concentrated, and submitted to flash chromatography on silica gel (1:1 hexane-ether) to give 4-methoxy-2-(2-methoxy-4,6-dimethyl-phenyl)-6-methyl-5-nitro-pyrimidine. $^1$H NMR (CDCl$_3$, 400 MHz) δ 2.08 (s, 3H), 2.36 (s, 3H), 2.60 (s, 3H), 3.73 (s, 3H), 4.08 (s, 3H), 6.62 (s, 1H), 6.68 (s, 1H); MS (CI) 304.

B: 4-Methoxy-2-(2-methoxy-4,6-dimethyl-phenyl)-6-methyl-pyrimidin-5-ylamine. A solution of 4-methoxy-2-(2-methoxy-4,6-dimethyl-phenyl)-6-methyl-5-nitro-pyrimidine (6.2 g, 20.4 mmol) in methanol (150 mL) is hydrogenated in the presence of palladium catalyst (5%/C, 1 g) at 1 atm of hydrogen (balloon). After 1 h the reaction mixture is purged with nitrogen, the catalyst is removed by filtration through celite, and the solvent evaporated to produce 4-methoxy-2-(2-methoxy-4,6-dimethyl-phenyl)-6-methyl-5-nitro-pyrimidine as a white solid. $^1$H NMR (CDCl$_3$, 400 MHz) δ 2.02 (s, 3H), 2.30 (s, 3H), 2.40 (s, 3H), 3.50 (br, 2H), 3.72 (s, 3H), 3.98 (s, 3H), 6.60 (s, 1H), 6.68 (s, 1H).

C: [4-Methoxy-2-(2-methoxy-4,6-dimethyl-phenyl)-6-methyl-pyrimidin-5-yl]-dipropylamine. To a solution of 4-methoxy-2-(2-methoxy-4,6-dimethyl-phenyl)-6-methyl-pyrimidin-5-ylamine (2.5 g, 9.1 mmol) in 1,2-dichloroethane (120 mL) is added propionaldehyde (2.0 mL) and glacial acetic acid (2.2 mL). After 10 minutes sodium triacetoxyborohydride (9.0 g) is added in one portion. After 3 h the volatiles are removed by rotary evaporation. The residue is partitioned between ethyl acetate and saturated aqueous sodium bicarbonate, the layers are separated and the aqueous layer further extracted with ethyl acetate. The combined organics are washed with water, brine, dried (magnesium sulfate), filtered and concentrated to give [4-methoxy-2-(2-methoxy-4,6-dimethyl-phenyl)-6-methyl-pyrimidin-5yl]-nitro-pyrimidine. $^1$H NMR (CDCl$_3$, 400 MHz) δ 0.89 (t, 6H), 1.40 (m, 4H), 2.05 (s, 3H), 2.33 (s, 3H), 2.53 (s, 3H), 2.95 (t, 4H), 3.73 (s, 3H), 3.93 (s, 3H), 6.62 (s, 1H), 6.67 (s, 1H).

D. 5-Dipropylamino-2-(2-methoxy-4,6-dimethyl-phenyl)-6-methyl-3H-pyrimidin-4-one. A stirred solution of [4-methoxy-2-(2-methoxy-4,6-dimethyl-phenyl)-6-methyl-pyrimidin-5-yl]-dipropyl-amine (3.45 g; 9.7 mmol) in concentrated aqueous hydrochloric acid (23 mL) is stirred at 100° C. (oil bath temperature) for 2 h. After cooling down to room temperature, the reaction mixture is poured onto ice-water, and made alkaline with a cold solution of concentrated aqueous ammonia. A precipitate is formed, and the supernatant liquid separated by filtration. The precipitate is dissolved in ethyl acetate, and the resulting solution washed with water until neutral pH of the aqueous phase. The organic solution is dried (magnesium sulfate), and the solvent evaporated under reduced pressure to yield 5-dipropylamino-2-(2-methoxy-4,6-dimethyl-phenyl)-6-methyl-5-nitro-pyrimidine as an off-white solid: $^1$H NMR (CDCl$_3$, 400 MHz) δ 0.89 (t, 6H), 1.43 (m, 4H), 2.27 (s, 3H), 2.34 (s, 3H), 2.43 (s, 3H), 3.01 (t, 4H), 3.78 (s, 3H), 6.61 (s, 1H), 6.71 (s, 1H), 9.26 (br, 1H); MS (CI) 344.

E: 5-Dipropylamino-2-(2-methoxy-4,6-dimethyl-phenyl)-3,6-dimethyl-3H-pyrimidin-4-one. A solution of 5-dipropylamino-2-(2-methoxy-4,6-dimethyl-phenyl)-6-methyl-3H-pyrimidin-4-one (130 mg, 0.33 mmol) in anhydrous DMSO (1.0 mL) is added to a clear solution of NaH (40 mg, 60% in mineral oil, 1.0 mmol) in anhydrous DMSO (5 mL) under nitrogen atmosphere (balloon) at room temperature. After 90 min, methyl iodide is added (100 µl). The mixture is stirred at room temperature for 2 h, and the reaction quenched by addition of water. The crude is diluted with ethyl ether, and washed with brine. The organic fraction is dried (magnesium sulfate), and the residue submitted to flash chromatography, eluting with ethyl acetate: hexanes (1:3), to produce the title compound: $^1$H NMR (CDCl$_3$, 400 MHz) δ 0.90 (t, 6H), 1.42 (m, 4H), 2.08 (s, 3H), 2.35 (s, 3H), 2.41 (s, 3H), 3.01 (t, 4H), 3.21 (s, 3H), 3.75 (s, 3H), 6.61 (s, 1H), 6.71 (s, 1H); MS (CI) 358.

EX#s 2–26 in the Table I may be prepared following the methods described in Example 1.

TABLE I

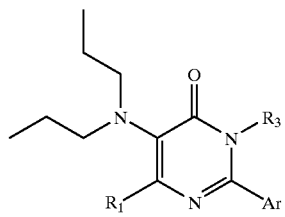

| Ex # | Ar | R$_1$ | R$_3$ | $^1$H-NMR | MS | Name |
|---|---|---|---|---|---|---|
| 2 | 6-methoxy-2,4-dimethyl-phenyl | Me | Et | 0.88(t, 6H), 1.05(t, 3H), 1.40(m, 4H), 2.05(s, 3H), 2.32(s, 3H), 2.37(s, 3H), 2.99(m, 4H), 3.64(m, 1H), 3.73(s, 3H), 3.81(m, 1H), 6.58(s, 1H), 6.67(s, 1H) | 372 | 5-Dipropylamino-2-(6-methoxy-2,4-dimethyl-phenyl)-3-ethyl-6-methyl-3H-pyrimidin-4-one |
| 3 | 6-methoxyl-2,4-dimethyl-phenyl | Me | n-Pr | 0.72(t, 3H), 0.87(t, 6H), 1.39(m, 6H), 2.05(s, 3H), 2.32(s, 3H), 2.37(s, 3H), 2.98(m, 4H), 3.51(m, 1H), 3.70(m, 1H), 3.72(s, 3H), 6.57(s, 1H), 6.67(s, 1H) | 386 | 5-Dipropylamino-2-(6-methoxy-2,4-dimethyl-phenyl)-3-propyl-6-methyl-3H-pyrimidin-4-one |
| 4 | 6-methoxy-2,4-dimethyl-phenyl | Me | i-Pr | 0.90(t, 6H), 1.32(m, 4H), 1.44(d, 3H), 1.52(d, 3H), 2.10(s, 3H), 2.35(s, 3H), | 386 | 5-Dipropylamino-2-(6-methoxy-2,4-dimethyl-phenyl)-3-iso-propyl-6-methyl-3H-pyrimidin-4-one |

TABLE I-continued

| Ex # | Ar | R₁ | R₃ | ¹H-NMR | MS | Name |
|---|---|---|---|---|---|---|
| | | | | 2.36(s, 3H), 2.99(m, 4H), 3.51(m, 1H), 3.70(m, 1H), 3.76(s, 3H), 3.97(m, 1H), 6.59(s, 1H), 6.70(s, 1H) | | |
| 5 | 6-methoxy-2,4-dimethyl-phenyl | Me | Bn | 0.92(t, 6H), 1.45(m, 4H), 2.34(s, 3H), 2.41(s, 3H), 3.07(m, 4H), 3.59(s, 3H), 4.57(d, 1H), 5.36(d, 1H), 6.55(s, 2H), 6.82(d, 2H), 7.15(m, 3H) | 435 | 5-Dipropylamino-2-(6-methoxy-2,4-dimethyl-phenyl)-3-butyl-6-methyl-3H-pyrimidin-4-one |
| 6 | 6-methoxy-2,4-dimethyl-phenyl | Me | —CH₂CH₂F | 0.89(t, 6H), 1.41(m, 4H), 2.11(s, 3H), 2.33(s, 3H), 2.39(s, 3H), 2.99(m, 4H), 3.73(s, 3H), 3.89(m, 1H), 4.17(m, 1H), 4.41(m, 1H), 4.63(m, 1H), 6.58(s, 1H), 6.70(s, 1H) | 390 | 5-Dipropylamino-2-(6-methoxy-2,4-dimethyl-phenyl)-3-(2-fluoro-ethyl)-6-methyl-3H-pyrimidin-4-one |
| 7 | 6-methoxy-2,4-dimethyl-phenyl | Me | —CH₂CF₃ | 0.89(t, 6H), 1.42(m, 4H), 2.15(s, 3H), 2.35(s, 3H), 2.41(s, 3H), 3.01(m, 4H), 3.76(s, 3H), 4.04(m, 1H), 4.94(m, 1H), 6.60(s, 1H), 6.74(s, 1H) | 427 | 5-Dipropylamino-2-(6-methoxy-2,4-dimethyl-phenyl)-3-(2,2,2-trifluoro-ethyl)-6-methyl-3H-pyrimidin-4-one |
| 8 | 6-methoxy-2,4-dimethyl-phenyl | Et | H | 0.87(t, 6H), 1.12(t, 3H), 1.38(m, 4H), 2.28(s, 3H), 2.33(s, 3H), 2.83(q, 2H), 2.90(m, 4H), 3.75(s, 3H), 6.59(s, 1H), 6.70(s, 1H), 10.81(br, 1H) | 358 | 5-Dipropylamino-2-(6-methoxy-2,4-dimethyl-phenyl)-6-methyl-3H-pyrimidin-4-one |
| 9 | 6-methoxy-2,4-dimethyl-phenyl | Et | Me | 0.85(t, 6H), 1.16(t, 3H), 1.40(m, 4H), 2.04(s, 3H), 2.36(s, 3H), 2.58(dq, 1H), 2.98(m, 4H), 3.02(dq, 1H), 3.18(s, 3H), 3.75(s, 3H), 6.60(s, 1H), 6.70(s, 1H) | 372 | 5-Dipropylamino-2-(6-methoxy-2,4-dimethyl-phenyl)-3-methyl-6-ethyl-3H-pyrimidin-4-one |
| 10 | 6-methoxy-2,4-dimethyl-phenyl | Et | Et | 0.90(t, 6H), 1.07(t, 3H), 1.16(t, 3H), 1.42(m, 4H), 2.08(s, 3H), 2.35(s, 3H), 2.57(m, 1H), 3.01(m, 5H), 3.64(m, 1H), 3.75(s, 3H), 3.87(m, 1H), 6.61(s, 1H), 6.71(s, 1H) | 386 | 5-Dipropylamino-2-(6-methoxy-2,4-dimethyl-phenyl)-3-ethyl-6-ethyl-3H-pyrimidin-4-one |
| 11 | 2,4,6-trimethylphenyl | Et | H | 0.84(t, 6H), 1.18(t, 3H), 1.38(m, 4H), 2.18(s, 6H), 2.28(s, 3H), 2.92(m, 6H), 7.85(s, 2H) | 342 | 5-Dipropylamino-2-(2,4,6-tri-methyl-phenyl)-6-ethyl-3H-pyrimidin-4-one |
| 12 | 2,4,6-trimethylphenyl | Me | H | 0.84(t, 6H), 1.36(m, 4H), 2.14(s, 6H), 2.28(s, 3H), 2.42(s, 3H), 2.95(m, 4H), 5.30(s, 1H), 7.85(s, 2H) | 328 | 5-Dipropylamino-2-(2,4,6-tri-methyl-phenyl)-6-methyl-3H-pyrimidin-4-one |
| 13 | 2,4,6-trimethylphenyl | Me | Et | 0.88(t, 6H), 1.05(t, 3H), 1.40(m, 4H), 2.06(s, 6H), 2.32(s, 3H), 2.39(s, 3H), 3.00(m, 4H), 3.72(q, 2H), 6.90(s, 2H) | 356 | 5-Dipropylamino-2-(2,4,6-tri-methyl-phenyl)-3-ethyl-6-methyl-3H-pyrimidin-4-one |
| 14 | 2,4,6-trimethylphenyl | Me | (CH₂-pyrrolidinyl group) | 0.88(t, 6H), 1.40(m, 4H), 1.62(br s, 4H), 2.06(s, 6H), 2.14(s, 3H), 2.32(br s, 2H), 2.37(s, 3H), 2.57(m, 4H), 2.98(m, 4H), 3.81(m, 2H), 6.83(s, 2H | 425 | 5-Dipropylamino-6-methyl-3-(2-pyrrolidin-1-yl-ethyl)-2-(2,4,6-trimethyl-phenyl)-3H-pyrimidin-4-one |

TABLE I-continued

| Ex # | Ar | $R_1$ | $R_3$ | $^1$H-NMR | MS | Name |
|---|---|---|---|---|---|---|
| 15 | 2,4-dichlorophenyl | Me | Et | 0.90(t, 6H), 1.12(t, 3H), 1.40(m, 4H), 2.38(s, 3H), 3.00(m, 4H), 3.45(dq, 1H), 4.15(dq, 1H), 7.38(m, 2H), 7.55(s, 1H) | 382 | 5-Dipropylamino-2-(2,4-dichloro-phenyl)-3-ethyl-6-methyl-3H-pyrimidin-4-one |
| 16 | 2,4-dimethoxyphenyl | Me | H | 0.84(t, 6H), 1.40(m, 4H), 2.42(s, 3H), 2.98(m, 4H), 3.83(s, 3H), 3.99(s, 3H), 6.47(s, 1H), 6.63(d, 1H), 8.40(d, 1H) | 346 | 5-Dipropylamino-2-(2,4-dimeth-oxy-phenyl)-6-methyl-3H-pyrimidin-4-one |
| 17 | 2,4-dimethoxyphenyl | Me | Me | 0.95(t, 6H), 1.42(m, 4H), 2.40(s, 3H), 3.00(m, 4H), 3.24(s, 3H), 3.78(s, 3H), 3.84(s, 3H), 6.54(s, 1H), 6.58(d, 1H), 7.24(d, 1H) | 360 | 5-Dipropylamino-2-(2,4-dimeth-oxy-phenyl)-3,6-dimethyl-3H-pyrimidin-4-one |
| 18 | 2,4-dimethoxyphenyl | Me | Et | 0.92(t, 6H), 1.05(t, 3H), 1.42(m, 4H), 2.38(s, 3H), 3.00(m, 4H), 3.46(dq, 1H), 3.78(s, 3H), 3.86(s, 3H), 4.15(dq, 1H), 6.52(s, 1H), 6.58(d, 1H), 7.28(d, 1H) | 376 | 5-Dipropylamino-2-(2,4-dimeth-oxy-phenyl)-3-ethyl-6-methyl-3H-pyrimidin-4-one |
| 19 | 2,4-dimethoxyphenyl | Me | n-Pr | 0.86(t, 6H), 0.94(t, 6H), 1.40–1.50(m, 6H), 2.38(s, 3H), 2.98(m, 4H), 3.36(m, 1H), 3.78(s, 3H), 3.84(s, 3H), 4.06(m, 1H), 6.45(s, 1H), 6.58(d, 1H), 7.26(d, 1H) | 390 | 5-Dipropylamino-2-(2,4-dimeth-oxy-phenyl)-3-propyl-6-methyl-3H-pyrimidin-4-one |
| 20 | 2,4-dimethoxyphenyl | Me | —CH$_2$-cyclopropyl | −0.05(m, 1H), 0.18(m, 1H), 0.38(m, 2H), 0.92(t, 6H), 1.42(m, 4H), 2.40(s, 3H), 3.00(m, 4H), 3.21(dd, 1H), 3.78(s, 3H), 3.84(s, 3H), 4.22(dd, 1H), 6.44(s, 1H), 6.58(d, 1H), 7.30(d, 1H) | 400 | 5-Dipropylamino-2-(2,4-dimeth-oxy-phenyl)-3-cyclpropyl-methyl-6-methyl-3H-pyrimidin-4-one |
| 21 | 2,4-dimethoxyphenyl | Me | —CH$_2$CH$_2$OMe | 0.92(t, 6H), 1.42(m, 4H), 2.40(s, 3H), 3.00(m, 4H), 3.18(s, 3H), 3.4–3.6(m, 2H), 3.65(dq, 1H), 3.80(s, 3H), 3.82(s, 3H), 4.37(dq, 1H), 6.44(s, 1H), 6.60(d, 1H), 7.24(d, 1H) | 404 | 5-Dipropylamino-2-(2,4-dimeth-oxy-phenyl)-3-(2-meth-oxy-ethyl)-6-methyl-3H-pyrimidin-4-one |
| 22 | 2-Methoxy, 6-trifluoro-methoxy phenyl | Me | H | | | 5-Dipropylamino-2-(2-meth-oxy-6-trifluoro-methoxy-phenyl)-6-methyl-3H-pyrimidin-4-one |
| 23 | 2-Methoxy, 6-trifluoro-methoxy phenyl | Me | —CH$_2$CH$_3$ | | | 5-Dipropylamino-2-(2-meth-oxy-6-trifluoro-methoxy-phenyl)-3-ethyl-6-methyl-3H-pyrimidin-4-one |
| 24 | 2,6-Dimethoxyphenyl | Me | methyl | | | 5-Dipropyl-amino-2-(2,6-dimethoxyphenyl)-3,6-di-methyl-3H-pyrimidin-4-one |
| 25 | 2,6-Dimethoxyphenyl | Me | —CH$_2$CH$_3$ | | | 5-Dipropyl-amino-2-(2,6-dimethoxy-phenyl)-3-ethyl-6-methyl-3H-pyrimidin-4-one |
| 26 | 2,6-Dimethoxyphenyl | Me | H | | | 5-Dipropyl-amino-2-(2,6-dimethoxy-phenyl)-6-methyl-3H-pyrimidin-4-one |

Example 27

5-(Cyclopropylmethyl-propyl-amino)-2-(2,4-dimethoxy-phenyl)-6-ethyl-3-(2-fluoro-ethyl)-3H-pyrimidin-4-one [Formula I: Ar=2,4-dimethoxyphenyl; $R_1$=$CH_2CH_3$; $R_2$=$N(CH_2CH_2CH_3)(CH_2$—◁); $R_3$=$CH_2CH_2F$]

A: [2-(2,4-Dimethoxy-phenyl)-4-methyl-6-methoxy-pyrimidin-5-yl]-amide. A solution of 2-(2,4-Dimethoxy-phenyl)-4-ethyl-6-methoxy-pyrimidin-5-ylamine (1.3 g, 4.72 mmol) in ethyl acetate (30 mL) was treated with triethylamine (606 mg, 6.0 mmol) and cyclopropylcarbonyl chloride (624 mg, 6 mmol), and stirred under nitrogen atmosphere at room temperature for 16 h. The reaction mixture was diluted with sodium bicarbonate (saturated solution) and partitioned between ethyl acetate and brine. The organic layer was separated, dried (magnesium sulfate) and the solvent evaporated under reduced pressure to yield the title compound, (1.42 g, 88%). $^1$H NMR (CDCl$_3$, 400 MHz) δ 0.84 (m, 2H), 1.10 (m, 2H), 1.62 (m, 1H), 2.42 (s, 3H), 3.86 (s, 6H), 4.02 (s, 3H), 6.58 (s, 1H), 6.60 (d, 1H), 7.00 (br, 1H), 7.86 (d, 1H); MS (CI) 344.

B: Cyclopropanecarboxylic acid [2-(2,4-dimethoxy-phenyl)-4-methyl-6-methoxy-pyrimidin-5-yl]-propyl-amide. A solution of cyclopropanecarboxylic acid [2-(2,4-dimethoxy-phenyl)-4-methyl-6-methoxy-pyrimidin-5-yl]-amide (1.3 g, 3.8 mmol) and iodoethane (1.02 g, 6.0 mmol) in anhydrous DMF (30 mL) is treated with sodium hydride (240 mg, 6.0 mmol) and heated at 60° C. for 3 h. The reaction mixture is cooled down to room temperature, and partitioned between ethyl acetate and sodium bicarbonate (saturated solution). The organic layer is washed with brine, dried, and the solvent removed under reduced pressure, to produce the title compound. $^1$H NMR (CDCl$_3$, 400 MHz) δ 0.60 (m, 2H), 0.85 (t, 6H), 1.02 (m, 2H), 1.20 (m, 1H), 1.56 (m, 2H), 2.44 (s, 3H), 3.46 (m, 2H), 3.84 (s, 3H), 3.86 (s, 3H), 4.02 (s, 3H), 6.58 (s, 1H), 6.60 (d, 1H), 7.90 (d, 1H); MS (CI) 386.

C: Cyclopropanecarboxylic acid [2-(2,4-dimethoxy-phenyl)-4-ethyl-6-methoxy-pyrimidin-5-yl]-propyl-amide. To a solution of LDA (8.0 mmol) in THF (35 mL) at −78° C. under nitrogen atmosphere is added cyclopropanecarboxylic acid [2-(2,4-dimethoxy-phenyl)-4-methyl-6-methoxy-pyrimidin-5-yl]-propyl-amide (2.6 g, 6.7 mmol). After 15 min methyl iodide (1.4 mL, 10 mmol) is added dropwise. An hour later the reaction is quenched by addition of water, and extracted into ethyl ether. The organic layer is washed, dried (magnesium sulfate) and the solvents removed under reduced pressure. Chromatographic purification is carried out on silica gel, eluting with hexanes:ethyl ether (1:1), yielding of title compound. $^1$H NMR (CDCl$_3$, 400 MHz) δ 0.60 (m, 2H), 0.85 (t, 6H), 1.20 (m, 1H), 1.28 (t, 3H), 1.56 (m, 2H), 2.78 (m, 2H), 3.46 (m, 2H), 3.84 (s, 3H), 3.86 (s, 3H), 4.02 (s, 3H), 6.58 (s, 1H), 6.60 (d, 1H), 7.98 (d, 1H).

D. Cyclopropyl-methyl-[2-(2,4-dimethoxy-phenyl)-4-ethyl-6-methoxy-pyrimidin-5-yl]-propyl-amine. To a solution of cyclopropanecarboxylic acid [2-(2,4-dimethoxy-phenyl)-4-ethyl-6-methoxy-pyrimidin-5-yl]-propyl-amide (397 mg, 1.0 mmol) in THF (8 mL) at 0° C. under nitrogen atmosphere is added DIBAL (1.0 mmol, 1M solution in hexanes, 1.0 mL). After 3 h at room temperature the reaction is quenched with ammonium chloride (saturated solution, 5 mL) and then neutralized with sodium hydroxide (4 M). The crude is extracted into ethyl ether, washed with brine, dried (magnesium sulfate) and the solvents removed under reduced pressure. The title compound is obtained as a yellow oil. $^1$H NMR (CDCl$_3$, 400 MHz) δ 0.00 (d, 1H), 0.38 (d, 1H), 0.80 (m, 1H), 0.85 (t, 6H), 1.28 (t, 3H), 1.4 (m, 1H), 2.80 (m, 1H), 2.92 (t, 2H), 3.02 (t, 2H), 3.84 (s, 3H), 3.86 (s, 3H), 4.00 (s, 3H), 6.57 (s, 1H), 6.59 (d, 1H), 7.82 (d, 1H); MS (CI) 387.

E. 5-(cyclopropylmethyl-propyl-amino)-2-(2,4-dimethoxy-phenyl)-6-ethyl-3H-pyrimidin-4-one. A stirred solution of cyclopropyl-methyl-[2-(2,4-dimethoxy-phenyl)-4-ethyl-6-methoxy-pyrimidin-5-yl]-propyl-amine (200 mg; 0.52 mmol) in concentrated aqueous hydrochloric acid (2.0 mL) is stirred at 100° C. (oil bath temperature) for 2 h. After cooling down to room temperature, the reaction mixture is poured onto ice-water, and made alkaline with a cold solution of concentrated aqueous ammonia. A precipitate is formed, and the supernatant liquid separated by filtration. The precipitate is dissolved in ethyl acetate, and the resulting solution washed with water until neutral pH of the aqueous phase. The organic solution is dried (magnesium sulfate), and the solvent evaporated under reduced pressure to yield 5-(cyclopropylmethyl-propyl-amino)-2-(2,4-dimethoxy-phenyl)-6-ethyl-3H-pyrimidin-4-one as an off-white solid. MS (CI) 372.

F: 5-(Cyclopropylmethyl-propyl-amino)-2-(2,4-dimethoxy-phenyl)-6-ethyl-3-(2-fluoro-ethyl)-3H-pyrimidin-4-one. A solution of 5-(cyclopropylmethyl-propyl-amino)-2-(2,4-dimethoxy-phenyl)-6-ethyl-3H-pyrimidin-4-one (173 mg, 0.46 mmol) is added to a clear solution of NaH (60 mg, 60% in mineral oil, 1.5 mmol) in anhydrous DMSO (4.0 mL) under nitrogen atmosphere (balloon) at room temperature. After 60 min, 1-fluoro-2-iodoethane is added (258 mg, 1.5 mmol). The mixture is stirred at room temperature for 2 h, and the reaction quenched by addition of water. The crude is diluted with ethyl ether, and washed with brine. The organic fraction is dried (magnesium sulfate), and the residue submitted to preparative thin layer chromatography, eluting with ethyl ether: hexanes (1:1), to produce the title compound. $^1$H NMR (CDCl$_3$, 400 MHz) δ 0.05 (d, 1H), 0.38 (d, 1H), 0.80 (m, 1H), 0.86 (t, 3H), 0.97 (t, 1H), 1.20 (t, 3H), 1.32 (t, 1H), 1.42 (m, 2H), 2.66 (m, 1H), 2.80 (q, 1H), 2.90 (m, 2H), 3.04 (m, 2H), 3.76 (s, 3H), 3.82 (s, 3H), 3.83 (m, 1H), 4.34–4.45 (m, 2H), 4.64 (m, 1H), 6.47 (s, 1H), 6.60 (d, 1H), 7.28 (d, 1H); MS (CI) 418.

EX#s 28–30 in the Table II may be prepared following the methods described in Example 27.

TABLE II

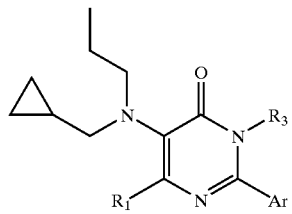

| Ex # | Ar | R₁ | R₂ | ¹H-NMR | MS | Name |
|---|---|---|---|---|---|---|
| 28 | 2,4-dimethoxyphenyl | Et | CH₂CH₂F | 0.03(d, 1H), 0.38 (d, 1H), 0.8(m, 1H), 0.89(t, 3H), 1.22(t, 3H), 1.41 (m, 2H), 2.11(s, 3H), 2.33(s, 3H), 2.39, 2.6–3.1(m, 6H), 3.78(s, 3H), 3.85(s, 3H), 4.3–4.7 (m, 4H), 6.45 (s, 1H), 6.60(d, 1H), 7.30(d, 1H) | 419 | 5-(Cyclopropylmethyl-propyl-amino)-2-(2,4-dimethoxy-phenyl)-3-(2-fluoro-ethyl)-6-ethyl-3H-pyrimidin-4-one |
| 29 | (2,4-dimethyl-6-(2-morpholin-4-yl-ethoxy)phenyl) | Et | H | 0.03(d, 1H), 0.38 (d, 1H), 0.8(m, 1H), 0.89(t, 3H), 1.22(t, 3H), 1.42 (m, 1H), 1.62(m, 1H), 2.25(s, 3H), 2.28(s, 3H), 2.45 (br 3H), 2.62(m, 3H), 2.90(m, 2H), 3.06(m, 1H), 3.12 (m, 1H), 3.5–3.6 (m, 4H), 4.26(m, 2H), 6.62(s, 1H), 6.78(s, 1H) | 470 | 5-(Cyclopropyl-methyl-propyl-amino)-2-[2,4-dimethyl-6-(2-morpholin-4-yl-ethoxy)-phenyl]-6-ethyl-3H-pyrimidin-4-one |
| 30 | (2,4-dimethyl-6-(2-morpholin-4-yl-ethoxy)phenyl) | Et | Et | 0.03(d, 1H), 0.38 (d, 1H), 0.8–1.5(m, 15H), 1.62(m, 1H), 2.06(s, 3H), 2.28(s, 3H), 2.40 (m, 2H), 2.45(br, 3H), 2.60(m, 3H), 2.95–3.08(m, 4H), 3.12(m, 1H), 3.5–3.6 (m, 4H), 3.85 (dq, 1H), 4.08(m, 2H), 4.12(dq, 1H), 6.58(s, 1H), 6.78(s, 1H) | 498 | 5-(Cyclopropylmethyl-propyl-amino)-2-[2,4-dimethyl-6-(2-morpholin-4-yl-ethoxy)-phenyl]-3,6-diethyl-3H-pyrimidin-4-one |

Example 31

Assay for CRF Receptor Binding Activity

As discussed above, the following assay is defined herein as a standard in vitro CRF receptor binding assay.

The pharmaceutical utility of compounds of this invention is indicated by the following assay for CRF1 receptor activity. The CRF receptor binding is performed using a modified version of the assay described by Grigoriadis and De Souza (*Methods in Neurosciences*, Vol. 5, 1991). IMR-32 human neuroblastoma cells, a cell-line that naturally expresses the CRF1 receptor, are grown in IMR-32 Medium, which consists of EMEM w/Earle's BSS (JRH Biosciences, Cat# 51411) plus, as supplements, 2 mM L-Glutamine, 10% Fetal Bovine Serum, 25 mM HEPES (pH 7.2), 1 mM Sodium Pyruvate and Non-Essential Amino Acids (JRH Biosciences, Cat# 58572). The cells are grown to confluence and split three times (all splits and harvest are carried out using NO-ZYME—JRH Biosciences, Cat# 59226). The cells are first split 1:2, incubated for 3 days and split 1:3, and finally incubated for 4 days and split 1:5. The cells are then incubated for an additional 4 days before being differentiated by treatment with 5-bromo-2'deoxyuridine (BrdU, Sigma, Cat# B9285). The medium is replaced every 3–4 days with IMR-32 medium w/2.5 uM BrdU and the cells are harvested after 10 days of BrdU treatment and washed with calcium and magnesium-free PBS.

To prepare receptor containing membranes cells are homogenized in wash buffer (50 mM Tris HCl, 10 mM MgCl₂, 2 mM EGTA, pH 7.4) and centrifuged at 48,000×g for 10 minutes at 4° C. The pellet is re-suspended in wash buffer and the homogenization and centrifugation steps are performed two additional times.

Membrane pellets (containing CRF receptors) are re-suspended in 50 mM Tris buffer pH 7.7 containing 10 mM $MgCl_2$ and 2 mM EDTA and centrifuged for 10 minutes at 48,000 g. Membranes are washed again and brought to a final concentration of 1500 ug/ml in binding buffer (Tris buffer above with 0.1% BSA, 15 mM bacitracin and 0.01 mg/ml aprotinin.). For the binding assay, 100 ul of the membrane preparation are added to 96 well microtube plates containing 100 ul of 125I1 CRF (SA 2200 Ci/mmol, final concentration of 100 pM) and 50 ul of test compound. Binding is carried out at room temperature for 2 hours. Plates are then harvested on a BRANDEL 96 well cell harvester and filters are counted for gamma emissions on a Wallac 1205 BETAPLATE liquid scintillation counter. Non-specific binding is defined by 1 mM cold CRF. $IC_{50}$ values are calculated with the non-linear curve fitting program RS/1 (BBN Software Products Corp., Cambridge, MA). The binding affinity for the compounds of Formula I expressed as $IC_{50}$ value, generally ranges from about 0.5 nanomolar to about 10 micromolar. Preferred compounds of Formula I exhibit $IC_{50}$ values of less than or equal to 1.5 micromolar, more preferred compounds of Formula I exhibit $IC_{50}$ values of less than 500 nanomolar, still more preferred compounds of Formula I exhibit $IC_{50}$ values of less than 100 nanomolar, and most preferred compound of Formula I exhibit $IC_{50}$ values of less than 10 nanomolar. The compounds shown in Examples 1–33 have been tested in this assay and found to exhibit $IC_{50}$ values of less than or equal to 4 micromolar.

Example 32

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$. Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; $SR_1$ International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 33

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Examples.

Example 34

Additional Aspects of Preferred Compounds of the Invention

The most preferred compounds of the invention are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of the invention at certain doses (i.e., doses yielding therapeutically effective in vivo concentrations or preferably doses of 10, 50, 100, 150, or 200 mg/kg administered parenterally or preferably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably preferably not more than 25%, and more preferably not more than 10% over matched untreated controls in dogs or other non-rodent mammals.

In yet another aspect such doses of such preferred compounds also preferably do not promote the release of liver enzymes (e.g., ALT, LDH, or AST) from hepatocytes in vivo. Preferably such doses do not elevate serum levels of such enzymes by more than 100%, preferably not by more than 75% and more preferably not by more than 50% over matched untreated controls in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes into culture medium in vitro above baseline levels seen in media from untreated cells.

Because side effects are often due to undesirable receptor activation or antagonism, preferred compounds of the invention exert their receptor-modulatory effects with high selectivity. This means that they do not bind to certain other receptors (other than CRF receptors) with high affinity, but rather only bind to, activate, or inhibit the activity of such other receptors with affinity constants of greater than 100 nanomolar, preferably greater than 1 micromolar, more preferably greater than 10 micromolar and most preferably greater than 100 micromolar. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL-8 receptors. The group of other receptors to which preferred compounds do not bind with high affinity also includes GABAA receptors, bioactive peptide receptors (including NPY and VIP receptors), neurokinin receptors, bradykinin receptors (e.g., BK1 receptors and BK2 receptors), and hormone receptors (including thyrotropin releasing hormone receptors and melanocyte-concentrating hormone receptors).

Example 34a

Absence of Sodium Ion Channel Activity

Preferred compounds of the invention do not exhibit activity as sodium ion channel blockers. Sodium channel activity may be measured a standard in vitro sodium channel binding assays such as the assay given by Brown et al. (*J. Neurosci.* 1986, 265, 17995–18004). Preferred compounds of the invention exhibit less than 15 percent inhibition, and more preferably less than 10 percent inhibition, of sodium channel specific ligand binding when present at a concentration of 4 uM. The sodium ion channel specific ligand used may be labeled batrachotoxinin, tetrodotoxin, or saxitoxin. Such assays, including the assay of Brown referred to above, are performed as a commercial service by CEREP, Inc., Redmond, Wash.

Alternatively, sodium ion channel activity may be measured in vivo in an assay of anti-epileptic activity. Anti-epileptic activity of compounds may be measured by the ability of the compounds to inhibit hind limb extension in the supra maximal electro shock model. Male Han Wistar rats (150–200 mg) are dosed i.p. with a suspension of 1 to 20 mg of test compound in 0.25% methylcellulose 2 hr. prior to test. A visual observation is carried out just prior to testing for the presence of ataxia. Using auricular electrodes a current of 200 mA, duration 200 millisec, is applied and the presence or absence of hind limb extension is noted. Preferred compounds of the invention do not exhibit significant anti-epileptic activity at the p<0.1 level of significance or more preferably at the p<0.05 level of significance as measured using a standard parametric assay of statistical significance such as a student's T test.

Example 34b

Microsomal in Vitro Half-life

Compound half-life values ($t_{1/2}$ values) may be determined via the following standard liver microsomal half-life assay. Pooled Human liver microsomes are obtained from XenoTech LLC, 3800 Cambridge St. Kansas's City, Kans., 66103 (catalog # H0610). Such liver microsomes may also be obtained from In Vitro Technologies, 1450 South Rolling Road, Baltamore, Md. 21227, or from Tissue Transformation Technologies, Edison Corporate Center, 175 May Street, Suite 600, Edison, N.J. 08837. Reactions are preformed as follows:
Reagents:
Phosphate buffer: 19 mL 0.1 M $NaH_2PO_4$, 81 mL 0.1 $Na_2HPO_4$, adjusted to pH 7.4 with $H_3PO_4$.
CoFactor Mixture: 16.2 mg NADP, 45.4 mg Glucose-6-phosphate in 4 mL 100 mM $MgCl_2$.
Glucose-6-phosphate dehydrogenase: 214.3 ul glucose-6-phosphate dehydrogenase suspension (Boehringer-Manheim catalog no. 0737224, distributed by Roche Molecular Biochemicals, 9115 Hague Road, P.O. Box 50414, Indianapolis, Id. 46250) is diluted into 1285.7 ul distilled water.

Starting Reaction Mixture: 3 mL CoFactor Mixture, 1.2 mL Glucose-6-phosphate dehydrogenase.
Reaction:

6 test reactions are prepared, each containing 25 ul microsomes, 5 ul of a 100 uM solution of test compound, and 399 ul 0.1 M phosphate buffer. A seventh reaction is prepared as a positive control containing 25 ul microsomes, 399 ul 0.1 M phosphate buffer, and 5 ul of a 100 uM solution of a compound with known metabolic properties (e.g. DIAZEPAM or CLOZEPINE). Reactions are preincubated at 39° C. for 10 minutes. 71 ul Starting Reaction Mixture is added to 5 of the 6 test reactions and to the positive control, 71 ul 100 mM $MgCl_2$ is added to the sixth test reaction, which is used as a negative control. At each time point (0, 1, 3, 5, and 10 minutes) 75 ul of each reaction mix is pipetted into a well of a 96-well deep-well plate containing 75 ul ice-cold acetonitrile. Samples are vortexed and centrifuged 10 minutes at 3500 rpm (Sorval T 6000D centrifuge, H1000B rotor). 75 ul of supernatant from each reaction is transferred to a well of a 96-well plate containing 150 ul of a 0.5 uM solution of a compound with a known LCMS profile (internal standard) per well. LCMS analysis of each sample is carried out and the amount of unmetabolized test compound is measured as AUC, compound concentration vs time is plotted, and the $t_{1/2}$ value of the test compound is extrapolated.

Preferred compounds of the invention exhibit in vitro $t_{1/2}$ values of greater than 10 minutes and less than 4 hours. Most preferred compounds of the invention exhibit in vitro $t_{1/2}$ values of between 30 minutes and 1 hour in human liver microsomes.

Example 34c

MDCK Toxicity Assay

Compounds causing acute cytotoxicity will decrease ATP production by Madin Darby canine kidney (MDCK) cells in the following assay.

MDCK cells, ATCC no. CCL-34 (American Type Culture Collection, Manassas, Va.) are maintained in sterile conditions following the instructions in the ATCC production information sheet. The PACKARD, (Meriden, Conn.) ATP-LITE-M Luminescent ATP detection kit, product no. 6016941, allows measurement ATP production in MDCK cells.

Prior to assay 1 ul of test compound or control sample is pipetted into PACKARD (Meriden, Conn.) clear bottom 96-well plates. Test compounds and control samples are diluted in DMSO to give final concentration in the assay of 10 micromolar, 100 micromolar, or 200 micromolar. Control samples are drug or other compounds having known toxicity properties.

Confluent MDCK cells are trypsinized, harvested, and diluted to a concentration of $0.1 \times 10^6$ cells/ml with warm (37° C.) VITACELL Minimum Essential Medium Eagle (ATCC catalog # 30-2003). 100 ul of cells in medium is pipetted into each of all but five wells of each 96-well plate. Warm medium without cells (100 ul) is pipetted in the remaining five wells of each plate to provide standard curve control wells. These wells, to which no cells are added, are used to determine the standard curve. The plates are then incubated at 37° C. under 95% $O_2$, 5% $CO_2$ for 2 hours with constant shaking. After incubation, 50 ul of mammalian cell lysis solution is added per well, the wells are covered with PACKARD TOPSEAL stickers, and plates are shaken at approximately 700 rpm on a suitable shaker for 2 minutes.

During the incubation, PACKARD ATP LITE-M reagents are allowed to equilibrate to room temperature. Once equilibrated the lyophilized substrate solution is reconstituted in 5.5 mls of substrate buffer solution (from kit). Lyophilized ATP standard solution is reconstituted in deionized water to give a 10 mM stock. For the five control wells, 10 ul of serially diluted PACKARD standard is added to each of the five standard curve control wells to yield a final concentration in each subsequent well of 200 nM, 100 nM, 50 nM, 25 nM, and 12.5 nM.

PACKARD substrate solution (50 ul) is added to all wells. Wells are covered with PACKARD TOPSEAL stickers, and plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter, e.g. PACKARD TOPCOUNT Microplate Scintillation and Luminesense Counter or TECAN SPECTRAFLUOR PLUS.

Luminescence values at each drug concentration are compared to the values computed from the standard curve for that concentration. Preferred test compounds exhibit luminescence values 80% or more of the standard, or preferably 90% or more of the standard, when a 10 micromolar (uM) concentration of the test compound is used. When a 100 uM concentration of the test compound is used, preferred test compounds exhibit luminescence values 50% or more of the standard, or more preferably 80% or more of the standard.

What is claimed is:

1. A compound of Formula I-a:

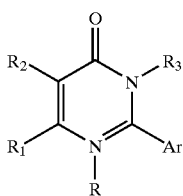

Formula I-a or a pharmaceutically acceptable salt thereof, wherein:

Ar is chosen from phenyl optionally substituted with up to 5 groups $R_A$, naphthyl optionally substituted with up to 5 groups $R_A$, and heteroaryl optionally substituted with up to 5 groups $R_A$, said heteroaryl having from 1 to 3 rings, 5 to 7 ring members in each ring and, in at least one of said rings, from 1 to about 3 heteroatoms selected from the group consisting of N, O, and S;

R is oxygen, methyl, or absent;

$R_1$ is chosen from hydrogen, halogen, hydroxy, cyano, nitro, haloalkyl, haloalkoxy, alkyl, alkenyl, alkynyl, alkoxy, cycloalkyl, (cycloalkyl)alkyl, mono- and di-aminoalkyl, and —S(O)$_n$alkyl;

$R_2$ is $XR_C$ or Y;

$R_3$ is chosen from hydrogen, haloalkyl, haloalkoxy, alkyl, alkenyl, alkynyl, alkoxy, cycloalkyl, (cycloalkyl)alkyl, mono- and di-aminoalkyl, and —S(O)$_n$alkyl, —CH$_2$R$_C$, —CHR$_D$R$_C$, —OR$_C$, —C(=O)R$_C$, NHR$_C$—NH$_D$R$_C$, —C(=O)NHR$_C$, —C(=O)NR$_D$R$_C$, —S(O)$_n$NHR$_C$, —S(O)$_n$NR$_D$R$_C$, —NHC(=O)R$_C$, —NR$_D$C(=O)R$_C$, and Y;

$R_A$ is independently selected at each occurrence from halogen, cyano, nitro, haloalkyl, haloalkoxy, hydroxy, amino, alkyl substituted with 0–2 $R_B$, alkenyl substituted with 0–2 $R_B$, alkynyl substituted with 0–2 $R_B$, cycloalkyl substituted with 0–2 $R_B$, (cycloalkyl)alkyl substituted with 0–2 $R_B$, alkoxy substituted with 0–2 $R_B$, —N—H(alkyl) substituted with 0–2 $R_B$, —N(alkyl)(alkyl) of which each alkyl is independently substituted with 0–2 $R_B$, —XR$_C$, and Y;

$R_B$ is independently selected at each occurrence from the group consisting of halogen, hydroxy, cyano, amino, alkyl, —O(alkyl), —NH(alkyl), —N(alkyl)(alkyl), —S(O)$_n$(alkyl), haloalkyl, haloalkoxy, CO(alkyl), CONH(alkyl), CON(alkyl)(alkyl), —XR$_C$, and Y;

$R_C$ and $R_D$, which may be the same or different, are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds, each of which 1 to 8 carbon atoms may be further substituted with one or more substituent(s) independently selected from hydroxy, halogen, cyano, amino, C$_1$–C$_6$alkoxy, —NH(C$_1$–C$_6$alkyl), —N(C$_1$–C$_6$alkyl)(C$_1$–C$_6$alkyl), —NHC(=O)(C$_1$–C$_6$alkyl), —N(C$_1$–C$_6$alkyl)C(=O)(C$_1$–C$_6$alkyl), —NHS(O)$_n$(C$_1$–C$_6$alkyl), —S(O)$_n$(C$_1$–C$_6$alkyl), —S(O)$_n$NH(C$_1$–C$_6$alkyl), —S(O)$_n$N(C$_1$–C$_6$alkyl)(C$_1$–C$_6$alkyl), and Z;

X is independently selected at each occurrence from the group consisting of —CH$_2$—, —CHR$_D$—, —O—, —C(=O)—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, —OSiH$_2$—, —OSiH(C$_1$–C$_4$alkyl)-, —OSi(C$_1$–C$_4$alkyl)(C$_1$–C$_4$alkyl)-, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, alkyl, —O(alkyl), —NH(alkyl), —N(alkyl)(alkyl), and —S(O)$_n$(alkyl), wherein said 3- to 7-memberered heterocyclic groups contain one or more heteroatom(s) independently selected from N, O, and S, with the point of attachment being either carbon or nitrogen; and n is independently selected at each occurrence from 0, 1, and 2;

provided that $R_1$ is not hydrogen, alkyl, or trifluoromethyl when $R_2$ is hydrogen, alkyl or alkenyl.

2. A compound or salt according to claim 1 wherein:

Ar and R are as defined in claim 1;

$R_1$ is chosen from hydrogen, halogen, hydroxy, cyano, nitro, halo(C$_1$–C$_6$)alkyl, halo(C$_1$–C$_6$)alkoxy, C$_1$–C$_6$alkyl, C$_2$–C$_6$alkenyl, C$_2$–C$_6$alkynyl, C$_1$–C$_6$alkoxy, C$_3$–C$_7$cycloalkyl, (C$_3$–C$_7$cycloalkyl) C$_1$–C$_4$alkyl, mono- and di-C$_1$–C$_6$)alkyl-amino, and —S(O)$_n$(C$_1$–C$_6$)alkyl;

$R_2$ is $XR_C$ or Y;

$R_3$ is chosen from hydrogen, halo(C$_1$–C$_6$)alkyl, halo (C$_1$–C$_6$)alkoxy, C$_1$–C$_6$alkyl, C$_2$–C$_6$alkenyl, C$_2$–C$_6$alkynyl, C$_1$–C$_6$alkoxy, C$_3$–C$_7$cycloalkyl, (C$_3$–C$_7$cycloalkyl) C$_1$–C$_4$alkyl, mono- and di-(C$_1$–C$_4$) alkylamino, and —S(O)$_n$(C$_1$–C$_6$)alkyl, —CH$_2$R$_C$, —CHR$_D$R$_C$, —OR$_C$, —C(=O)R$_C$, —NHR$_C$, —NR$_D$R$_C$, —C(=O)NHR$_C$, —C(=O)NR$_D$R$_C$, —S(O)$_n$NHR$_C$, —S(O)$_n$NR$_D$R$_C$, —NHC(=O)R$_C$, —NR$_D$C(=O)R$_C$, and Y;

R$_A$ is independently selected at each occurrence from halogen, cyano, nitro, halo(C$_1$–C$_6$)alkyl, halo(C$_1$–C$_6$) alkoxy, hydroxy, amino, C$_1$–C$_6$alkyl substituted with 0–2 R$_B$, C$_2$–C$_6$alkenyl substituted with 0–2 R$_B$, C$_2$–C$_6$alkynyl substituted with 0–2 R$_B$, C$_3$–C$_7$cycloalkyl substituted with 0–2 R$_B$, (C$_3$–C$_7$cycloalkyl) C$_1$–C$_4$alkyl substituted with 0–2 R$_B$, C$_1$–C$_6$alkoxy substituted with 0–2 R$_B$, —NH (C$_1$–C$_6$alkyl) substituted with 0–2 R$_B$, —N(C$_1$–C$_6$alkyl)(C$_1$–C$_6$alkyl) of which each C$_1$–C$_6$alkyl is independently substituted with 0–2 R$_B$, —XR$_C$, and Y;

R$_B$ is independently selected at each occurrence from the group consisting of:
i) halogen, hydroxy, cyano, amino, C$_1$–C$_4$alkyl, —O(C$_1$–C$_4$alkyl), —NH(C$_1$–C$_4$alkyl), —N(C$_1$–C$_4$alkyl)(C$_1$–C$_4$alkyl), —S(O)$_n$(alkyl), halo (C$_1$–C$_4$)alkyl, halo(C$_1$–C$_4$)alkoxy, CO(C$_1$–C$_4$alkyl), CONH(C$_1$–C$_4$alkyl), CON(C$_1$–C$_4$alkyl)(C$_1$–C$_4$alkyl), —XR$_C$, and
ii) morpholino, pyrrolidino, piperidino, thiomorpholino, and piperazino, each of which is optionally substituted with up to three substituents independently chosen from hydroxy, halogen, alkyl and alkoxy;

R$_C$ and R$_D$, which may be the same or different, are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds, each of which 1 to 8 carbon atoms may be further substituted with one or more substituent(s) independently selected from hydroxy, halogen, cyano, amino, C$_1$–C$_6$alkoxy, —NH(C$_1$–C$_6$alkyl), —N(C$_1$–C$_6$alkyl)(C$_1$–C$_6$alkyl), —NHC(=O)(C$_1$–C$_6$alkyl), —N(C$_1$–C$_6$alkyl)C(=O)(C$_1$–C$_6$alkyl), —NHS(O)$_n$(C$_1$–C$_6$alkyl), —S(O)$_n$—(C$_1$–C$_6$alkyl), —S(O)$_n$NH(C$_1$–C$_6$alkyl), —S(O)$_n$N(C$_1$–C$_6$alkyl)(C$_1$–C$_6$alkyl), and Z;

X is independently selected at each occurrence from the group consisting of —CH$_2$—, —CHR$_D$—, —O—, —C(=O)—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, —OSiH$_2$—, —OSiH(C$_1$–C$_4$alkyl)-, —OSi(C$_1$–C$_4$alkyl)(C$_1$–C$_4$alkyl)-, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, C$_1$–C$_4$alkyl, —O(C$_1$–C$_4$alkyl), —NH(C$_1$–C$_4$alkyl), —N(C$_1$–C$_4$alkyl)(C$_1$–C$_4$alkyl), and —S(O)$_n$(alkyl),
wherein said 3- to 7-memberered heterocyclic groups contain one or more heteroatom(s) independently selected from N, O, and S, with the point of attachment being either carbon or nitrogen; and n is independently selected at each occurrence from 0, 1, and 2;

provided that R$_1$ is not hydrogen, alkyl, or trifluoromethyl when R$_2$ is hydrogen, alkyl or alkenyl.

3. A compound or salt according to claim 2 wherein:

R is absent;

Ar is chosen from phenyl, naphthyl, pyridyl, pyrimidinyl, pyrazinyl, pyridizinyl, thienyl, thiazolyl, oxazolyl, isoxazolyl, pyrrolyl, furanyl, and triazolyl, each of which is optionally substituted with up to 5 independently chosen groups R$_A$, wherein at least one position of said phenyl that is ortho or para to the point of attachment of Ar in Formula I is substituted.

4. A compound or salt according to claim 2, wherein

R is absent;

Ar is chosen from phenyl, naphthyl, and pyridyl, each of which is substituted with from 1 to 5 independently chosen groups R$_A$, wherein at least one position of Ar that is ortho or para to the point of attachment of Ar in Formula I is substituted.

5. A compound or salt according to claim 2, wherein

R is absent;

Ar is phenyl substituted with from 1 to 5 independently chosen groups R$_A$, wherein at least one position of Ar that is ortho or para to the point of attachment of Ar in Formula I is substituted.

6. A compound or salt according to claim 2, wherein

R is absent;

Ar is phenyl substituted with from 1 to 5 independently chosen groups R$_A$, wherein at least one position of Ar that is ortho or para to the point of attachment of Ar in Formula I is substituted;

R$_1$ is selected from hydrogen, halogen, C$_1$–C$_4$alkyl, C$_1$–C$_4$alkoxy, halo(C$_1$–C$_2$)alkyl, and halo(C$_1$–C$_2$) alkoxy; and R$_3$ is selected from halogen, C$_1$–C$_6$alkyl, C$_1$–C$_6$alkoxy, halo(C$_1$–C$_4$)alkyl, halo(C$_1$–C$_4$)alkoxy, (C$_3$–C$_7$cycloalkyl)C$_1$–C$_4$alkyl, pyrrolidin-1-yl(C$_1$–C$_4$) alkyl, piperidin-1-yl(C$_1$–C$_4$)alkyl, piperazin-1-yl (C$_1$–C$_4$)alkyl, morpholin-4-yl(C$_1$–C$_4$)alkyl, and thiomorpholin-4-yl(C$_1$–C$_4$)alkyl.

7. A compound or salt according to claim 2, wherein

R is absent;

Ar is phenyl substituted with from 1 to 5 independently chosen groups R$_A$, wherein at least one position of Ar that is ortho or para to the point of attachment of Ar in Formula I is substituted; and R$_C$ and R$_D$, which may be the same or different, are independently selected at each occurrence from:
hydrogen, and straight, branched, and cyclic alkyl groups, and (cycloalkyl)alkyl groups, said straight, branched, and cyclic alkyl groups, and (cycloalkyl) alkyl groups consist of 1 to 8 carbon atoms, and contain zero or one or more double or triple bonds.

8. A compound or salt according to claim 2, wherein

R is absent;

Ar is phenyl substituted with from 1 to 5 independently chosen groups R$_A$, wherein at least one position of Ar that is ortho or para to the point of attachment of Ar in Formula I is substituted;

R$_1$ is selected from hydrogen, halogen, C$_1$–C$_4$alkyl, C$_1$–C$_4$alkoxy, halo(C$_1$–C$_2$)alkyl, and halo(C$_1$–C$_2$) alkoxy;

R$_3$ is selected from hydrogen, halogen, C$_1$–C$_6$alkyl, C$_1$–C$_6$alkoxy, halo(C$_1$–C$_4$)alkyl, halo(C$_1$–C$_4$)alkoxy, (C$_3$–C$_7$cycloalkyl)C$_1$–C$_4$alkyl, pyrrolidin-1-yl(C$_1$–C$_4$)

alkyl, piperidin-1-yl($C_1$–$C_4$)alkyl, piperazin-1-yl ($C_1$–$C_4$)alkyl, morpholin-4-yl($C_1$–$C_4$)alkyl, and thiomorpholin-4-yl($C_1$–$C_4$)alkyl; and $R_C$ and $R_D$, which may be the same or different, are independently selected at each occurrence from:
hydrogen, and straight, branched, and cyclic alkyl groups, and (cycloalkyl)alkyl groups, said straight, branched, and cyclic alkyl groups, and (cycloalkyl) alkyl groups consist of 1 to 8 carbon atoms, and contain zero or one or more double or triple bonds.

9. A compound or salt according to claim 2, of Formula II

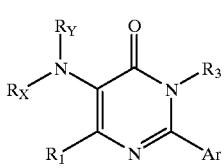

Formula II wherein:

$R_X$ and $R_Y$ are independently chosen from hydrogen, $C_1$–$C_6$alkyl$_1$, and ($C_3$–$C_7$cycloalkyl$_2$)$C_1$–$C_4$alkyl$_1$;
where each alkyl$_1$ is independently straight, branched, or cyclic, contains zero or 1 or more double or triple bonds, and is optionally substituted with one or more substituents independently chosen from halogen, hydroxy, amino, oxo, cyano, $C_1$–$C_4$alkoxy, and mono- and di($C_1$–$C_4$)alkylamino,
where each $C_3$–$C_7$cycloalkyl$_2$ is optionally substituted by one or more substituents independently chosen from halogen, amino, hydroxy, oxo, cyano, $C_1$–$C_4$alkoxy, and mono- or di($C_1$–$C_4$)alkylamino, and $R_1$, $R_3$ and Ar are as defined in claim 3.

10. A compound or salt according to claim 2, of Formula II

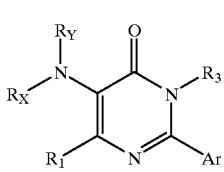

Formula II wherein:

$R_X$ and $R_Y$ are the same or different and are independently selected from hydrogen or straight, branched or cyclic alkyl groups, optionally containing one or more double or triple bonds or $NR_XR_Y$ taken in combination from a 3- to 7-memberered heterocyclic groups which optionally contain one or more heteroatom(s) independently selected from N, O, and S; and $R_1$, $R_3$ and Ar are as defined in claim 3.

11. A compound or salt according to claim 9, wherein:

Ar is phenyl, naphthyl, pyridyl, pyrimidinyl, pyrazinyl, pyridizinyl, thienyl, thiazolyl, oxazolyl, isoxazolyl, pyrrolyl, furanyl, and triazolyl, each of which is optionally substituted with up to 5 independently chosen groups $R_A$, wherein at least one position of said phenyl that is ortho or para to the point of attachment of Ar in Formula II is substituted.

12. A compound or salt according to claim 9, wherein:

Ar is chosen from phenyl, naphthyl, and pyridyl, each of which is substituted with from 1 to 5 independently chosen groups $R_A$, wherein at least one position of Ar that is ortho or para to the point of attachment of Ar in Formula II is substituted.

13. A compound or salt according to claim 9, wherein:

Ar is phenyl substituted with from 1 to 5 independently chosen groups $R_A$, wherein at least one position of Ar that is ortho or para to the point of attachment of Ar in Formula II is substituted;

$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy; and $R_3$ is selected from hydrogen, $C_1$–$C_6$alkyl, $C_1$–$C_6$alkoxy, halo($C_1$–$C_4$)alkyl, halo($C_1$–$C_4$)alkoxy, ($C_3$–$C_7$cycloalkyl)$C_1$–$C_4$alkyl, pyrrolidin-1-yl($C_1$–$C_4$) alkyl, piperidin-1-yl($C_1$–$C_4$)alkyl, piperazine-1-yl ($C_1$–$C_4$)alkyl, morpholin-4-yl($C_1$–$C_4$)alkyl, and thiomorpholin-4-yl($C_1$–$C_4$)alkyl.

14. A compound or salt according to claim 9, wherein:

Ar is phenyl substituted with from 1 to 5 independently chosen groups $R_A$, wherein at least one position of Ar that is ortho or para to the point of attachment of Ar in Formula II is substituted;

$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy; and $R_3$ is selected from $C_1$–$C_6$alkyl, $C_1$–$C_6$alkoxy, halo ($C_1$–$C_4$)alkyl, halo($C_1$–$C_4$)alkoxy, ($C_3$–$C_7$cycloalkyl)$C_1$–$C_4$alkyl, pyrrolidin-1-yl ($C_1$–$C_4$)alkyl, piperidin-1-yl($C_1$–$C_4$)alkyl, piperazine-1-yl($C_1$–$C_4$)alkyl, morpholin-4-yl ($C_1$–$C_4$)alkyl, and thiomorpholin-4-yl($C_1$–$C_4$)alkyl.

15. A compound or salt according to claim 9, wherein:

Ar is phenyl substituted with from 1 to 3 substituents independently chosen from:
halogen, cyano, nitro, halo($C_1$–$C_4$)alkyl, halo($C_1$–$C_4$) alkoxy, hydroxy, amino, $C_3$–$C_7$ cycloalkyl, ($C_3$–$C_7$cycloalkyl) ($C_1$–$C_4$)alkyl, $C_1$–$C_6$alkyl substituted with 0–2 $R_B$, $C_1$–$C_6$alkoxy substituted with 0–2 $R_B$, —NH($C_1$–$C_4$alkyl) substituted with 0–2 $R_B$, —N($C_1$–$C_4$alkyl)($C_1$–$C_4$alkyl) of which each $C_1$–$C_4$alkyl is independently substituted with 0–2 $R_B$, wherein at least one position of Ar that is ortho or para to the point of attachment of Ar in Formula II is substituted;

$R_B$ is independently selected at each occurrence from the group consisting of:

i) halogen, hydroxy, amino, $C_1$–$C_4$alkyl, —O($C_1$–$C_4$alkyl), —NH($C_1$–$C_4$alkyl), and —N($C_1$–$C_4$alkyl)($C_1$–$C_4$alkyl), and ii) morpholino, pyrrolidino, piperidino, thiomorpholino, and piperazino;

$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy; and $R_3$ is selected from $C_1$–$C_6$alkyl, $C_1$–$C_6$alkoxy, halo ($C_1$–$C_4$)alkyl, halo($C_1$–$C_4$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl ($C_1$–$C_4$)alkyl.

16. A compound or salt according to claim 9, wherein:

Ar is phenyl substituted with from 1 to 3 substituents independently chosen from:

halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl)$C_1$–$C_4$alkyl, mono and di($C_1$–$C_4$)alkylamino, $C_1$–$C_6$alkyl substituted with 0–2 $R_B$, $C_1$–$C_6$alkoxy substituted with 0–2 $R_B$,
wherein at least one position of Ar that is ortho or para to the point of attachment of Ar in Formula II is substituted;

$R_B$ is independently selected at each occurrence from the group consisting of:
i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and
ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$)alkoxy; and $R_3$ is selected from hydrogen, $C_1$–$C_4$alkyl, $C_1$–$C_4$alkoxy, halo($C_1$–$C_2$)alkyl, halo($C_1$–$C_2$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl.

17. A compound or salt according to claim 16 of the formula:

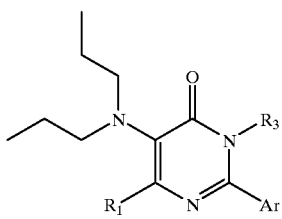

wherein $R_1$, $R_3$, and Ar are as defined for claim 16.

18. A compound or salt according to claim 16 of the formula:

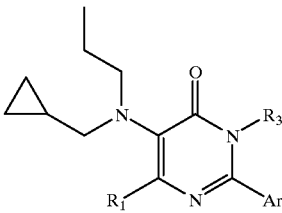

wherein $R_1$, $R_3$, and Ar are as defined for claim 16.

19. A compound or salt according to claim 16 of the formula:

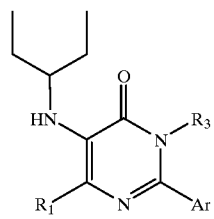

wherein $R_1$, $R_3$, and Ar are as defined for claim 16.

20. A compound or salt according to claim 2, of Formula IV

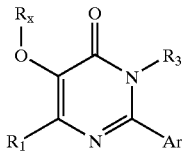

Formula IV wherein:
$R_X$ is chosen from $C_1$–$C_6$alkyl$_1$, ($C_3$–$C_7$cycloalkyl$_2$)$C_1$–$C_4$alkyl$_1$;
where each alkyl$_1$ is independently straight, branched, or cyclic, contains zero or 1 or more double or triple bonds, and is optionally substituted with one or more substituents independently chosen from halogen, hydroxy, amino, oxo, cyano, $C_1$–$C_4$alkoxy, and mono- or di($C_1$–$C_4$)alkylamino,
where each $C_3$–$C_7$cycloalkyl$_2$ is optionally substituted by one or more substituents independently chosen from halogen, amino, hydroxy, oxo, cyano, $C_1$–$C_4$alkoxy, and mono- or di($C_1$–$C_4$)alkylamino, and $R_1$, $R_3$ and Ar are as defined in claim 2.

21. A compound or salt according to claim 2, of Formula IV

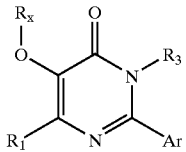

Formula IV wherein:
$R_X$ is selected from straight, branched or cyclic alkyl groups, optionally containing one or more double or triple bonds; and
$R_1$, $R_3$ and Ar are as defined in claim 2.

22. A compound or salt according to claim 20, wherein:
Ar is phenyl, naphthyl, pyridyl, pyrimidinyl, pyrazinyl, pyridizinyl, thienyl, thiazolyl, oxazolyl, isoxazolyl, pyrrolyl, furanyl, and triazolyl, each of which is optionally substituted with up to 5 independently chosen groups $R_A$ wherein at least one position of said phenyl that is ortho or para to the point of attachment of Ar in Formula IV is substituted.

23. A compound or salt according to claim 20, wherein:
Ar is chosen from phenyl, naphthyl, and pyridyl, each of which is substituted with from 1 to 5 independently chosen groups $R_A$, wherein at least one position of Ar that is ortho or para to the point of attachment of Ar in Formula VI is substituted.

24. A compound or salt according to claim 20, wherein:
Ar is phenyl substituted with from 1 to 5 independently chosen groups $R_A$, wherein at least one position of Ar that is ortho or para to the point of attachment of Ar in Formula IV is substituted;

$R_1$ is selected from hydrogen, halogen, $C_1$–$C_4$alkyl, $C_1$–$C_4$alkoxy, halo($C_1$–$C_2$)alkyl, and halo($C_1$–$C_2$)alkoxy; and $R_3$ is selected from $C_1$–$C_6$alkyl, $C_1$–$C_6$alkoxy, halo($C_1$–$C_4$)alkyl, halo($C_1$–$C_4$)alkoxy, ($C_3$–$C_7$cycloalkyl)

$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl ($C_1$–$C_4$)alkyl.

25. A compound or salt according to claim 20, wherein:

Ar is phenyl substituted with from 1 to 5 independently chosen groups $R_A$, wherein at least one position of Ar that is ortho or para to the point of attachment of Ar in Formula VI is substituted;

$R_1$ is selected from hydrogen, halogen, $C_1$–$C_4$alkyl, $C_1$–$C_4$alkoxy, halo($C_1$–$C_2$)alkyl, and halo($C_1$–$C_2$) alkoxy; and $R_3$ is selected from $C_1$–$C_6$alkyl, $C_1$–$C_6$alkoxy, halo ($C_1$–$C_4$)alkyl, halo($C_1$–$C_4$)alkoxy, ($C_3$–$C_7$cycloalkyl) $C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl ($C_1$–$C_4$)alkyl.

26. A compound or salt according to claim 20, wherein:

Ar is phenyl substituted with from 1 to 3 substituents independently chosen from:

halogen, cyano, nitro, halo($C_1$–$C_4$)alkyl, halo($C_1$–$C_4$) alkoxy, hydroxy, amino, $C_3$–$C_7$ cycloalkyl, ($C_3$–$C_7$cycloalkyl) ($C_1$–$C_4$)alkyl, $C_1$–$C_6$alkyl substituted with 0–2 $R_B$, $C_1$–$C_6$alkoxy substituted with 0–2 $R_B$, —NH($C_1$–$C_4$alkyl) substituted with 0–2 $R_B$, —N($C_1$–$C_4$alkyl)($C_1$–$C_4$alkyl) of which each $C_1$–$C_4$alkyl is independently substituted with 0–2 $R_B$, wherein at least one position of Ar that is ortho or para to the point of attachment of Ar in Formula VI is substituted;

$R_B$ is independently selected at each occurrence from the group consisting of:

i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and ii) morpholino, pyrrolidino, piperidino, thiomorpholino, and piperazino;

$R_1$ is selected from hydrogen, halogen, $C_1$–$C_4$alkyl, $C_1$–$C_4$alkoxy, halo($C_1$–$C_2$)alkyl, and halo($C_1$–$C_2$) alkoxy; and $R_3$ is selected from hydrogen, $C_1$–$C_6$alkyl, $C_1$–$C_6$alkoxy, halo($C_1$–$C_4$)alkyl, halo($C_1$–$C_4$)alkoxy, ($C_3$–$C_7$cycloalkyl)$C_1$–$C_4$alkyl, pyrrolidin-1-yl($C_1$–$C_4$) alkyl, piperidin-1-yl($C_1$–$C_4$)alkyl, piperazin-1-yl ($C_1$–$C_4$)alkyl, morpholin-4-yl($C_1$–$C_4$)alkyl, and thiomorpholin-4-yl($C_1$–$C_4$)alkyl.

27. A compound or salt according to claim 20, wherein:

Ar is phenyl substituted with from 1 to 3 substituents independently chosen from:

halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl) $C_1$–$C_4$alkyl, mono and di($C_1$–$C_4$) alkylamino, $C_1$–$C_6$alkyl substituted with 0–2 $R_B$, $C_1$–$C_6$alkoxy substituted with 0–2 $R_B$, wherein at least one position of Ar that is ortho or para to the point of attachment of Ar in Formula VI is substituted;

$R_B$ is independently selected at each occurrence from the group consisting of:

i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$) alkoxy; and $R_3$ is selected from $C_1$–$C_4$alkyl, $C_1$–$C_4$alkoxy, halo ($C_1$–$C_2$)alkyl, halo($C_1$–$C_2$)alkoxy, ($C_3$–$C_7$cycloalkyl) $C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl ($C_1$–$C_4$)alkyl.

28. A compound or salt according to claim 20 of the formula:

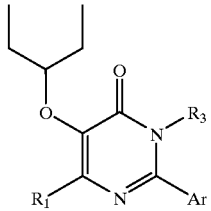

wherein:

Ar is phenyl substituted with from 1 to 3 substituents independently chosen from:

halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl) $C_1$–$C_4$alkyl, mono and di($C_1$–$C_4$) alkylamino, $C_1$–$C_6$alkyl substituted with 0–2 $R_B$, $C_1$–$C_6$alkoxy substituted with 0–2 $R_B$, wherein at least one position of Ar that is ortho or para to the point of attachment of Ar in Formula VI is substituted;

$R_B$ is independently selected at each occurrence from the group consisting of:

i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$) alkoxy; and $R_3$ is selected from hydrogen, $C_1$–$C_4$alkyl, $C_1$–$C_4$alkoxy, halo($C_1$–$C_2$)alkyl, halo($C_1$–$C_2$)alkoxy, ($C_3$–$C_7$cycloalkyl)$C_1$–$C_4$alkyl, pyrrolidin-1-yl($C_1$–$C_4$) alkyl, piperidin-1-yl($C_1$–$C_4$)alkyl, piperazin-1-yl ($C_1$–$C_4$)alkyl, morpholin-4-yl($C_1$–$C_4$)alkyl, and thiomorpholin-4-yl($C_1$–$C_4$)alkyl.

29. A compound or salt according to claim 27 of the formula:

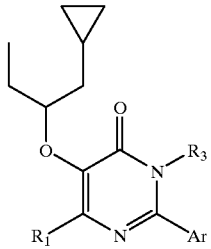

wherein:

Ar is phenyl substituted with from 1 to 3 substituents independently chosen from:

halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl) $C_1$–$C_4$alkyl, mono and di($C_1$–$C_4$) alkylamino, $C_1$–$C_6$alkyl substituted with 0–2 $R_B$, $C_1$–$C_6$alkoxy substituted with 0–2 $R_B$,
wherein at least one position of Ar that is ortho or para to the point of attachment of Ar in Formula IV is substituted;

$R_B$ is independently selected at each occurrence from the group consisting of:
i) halogen, hydroxy, amino, $C_1$–$C_4$alkyl, —O($C_1$–$C_4$alkyl), —NH($C_1$–$C_4$alkyl), —N($C_1$–$C_4$alkyl)($C_1$–$C_4$alkyl), and
ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$)alkoxy; and $R_3$ is selected from $C_1$–$C_4$alkyl, $C_1$–$C_4$alkoxy, halo($C_1$–$C_2$)alkyl,
halo($C_1$–$C_2$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl.

30. A compound or salt according to claim 2 of the Formula III:

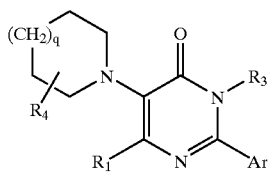

Formula III wherein $R_1$, $R_3$, and Ar are as defined in claim 3,
$R_4$ represents up to three substituents independently chosen from hydrogen, halogen, $C_1$–$C_6$alkyl, and $C_1$–$C_6$alkoxy; and
q is 0, 1, or 2.

31. A compound or salt according to claim 30, wherein:
Ar is phenyl substituted with from 1 to 3 substituents independently chosen from:
halogen, halo($C_1$–$C_2$)alkyl, halo($C_1$–$C_2$)alkoxy, hydroxy, amino, $C_3$–$C_7$cycloalkyl, ($C_3$–$C_7$cycloalkyl) $C_1$–$C_4$alkyl, mono and di($C_1$–$C_4$) alkylamino, $C_1$–$C_6$alkyl substituted with 0–2 $R_B$, $C_1$–$C_6$alkoxy substituted with 0–2 $R_B$,
wherein at least one position of Ar that is ortho or para to the point of attachment of Ar in Formula III is substituted;

$R_B$ is independently selected at each occurrence from the group consisting of:
i) halogen, hydroxy, amino, $C_1$–$C_4$alkyl, —O($C_1$–$C_4$alkyl), —NH($C_1$–$C_4$alkyl), and —N($C_1$–$C_4$alkyl)($C_1$–$C_4$alkyl), and
ii) morpholino, pyrrolidino, piperidino, thiomorpholino, and piperazino;

$R_1$ is selected from hydrogen, halogen, $C_1$–$C_2$alkyl, $C_1$–$C_2$alkoxy, halo($C_1$–$C_2$)alkyl, and halo($C_1$–$C_2$)alkoxy; and $R_3$ is selected from $C_1$–$C_4$alkyl, $C_1$–$C_4$alkoxy, halo($C_1$–$C_2$)alkyl, halo($C_1$–$C_2$)alkoxy, ($C_3$–$C_7$cycloalkyl)$C_1$–$C_4$alkyl, pyrrolidin-1-yl($C_1$–$C_4$)alkyl, piperidin-1-yl($C_1$–$C_4$)alkyl, piperazin-1-yl($C_1$–$C_4$)alkyl, morpholin-4-yl($C_1$–$C_4$)alkyl, and thiomorpholin-4-yl($C_1$–$C_4$)alkyl.

32. A compound or salt according to claim 2 wherein, in a standard in vitro CRF receptor binding assay the compound exhibits an $IC_{50}$ value for CRF receptors of less than or equal to 1 micromolar.

33. A compound or salt according to claim 2, wherein in a standard in vitro Na channel functional assay the compound does not show any detectable Na channel modulatory activity at the $p < 0.05$ level of significance in a standard parametric test of statistical significance.

34. A pharmaceutical composition comprising a pharmaceutically acceptable carrier and a compound or salt of claim 2.

35. A compound or salt according to Formula II

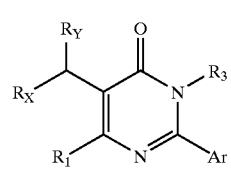

Formula II wherein:
$R_X$ and $R_Y$ are independently chosen from hydrogen, $C_1$–$C_6$alkyl$_1$, and ($C_3$–$C_7$cycloalkyl$_2$)$C_1$–$C_4$alkyl$_1$;
where each alkyl$_1$ is independently straight, branched, or cyclic, contains zero or 1 or more double or triple bonds, and is optionally substituted with one or more substituents independently chosen from halogen, hydroxy, amino, oxo, cyano, $C_1$–$C_4$alkoxy, and mono- and di($C_1$–$C_4$)alkylamino,
where each $C_3$–$C_7$cycloalkyl$_2$ is optionally substituted by one or more substituents independently chosen from halogen, amino, hydroxy, oxo, cyano, $C_1$–$C_4$alkoxy, and mono- or di($C_1$–$C_4$)alkylamino, and Ar is chosen from phenyl optionally substituted with up to 5 groups $R_A$, naphthyl optionally substituted with up to 5 groups $R_A$, and heteroaryl optionally substituted with up to 5 groups $R_A$, said heteroaryl having from 1 to 3 rings, 5 to 7 ring members in each ring and, in at least one of said rings, from 1 to about 3 heteroatoms selected from the group consisting of N, O, and S;

$R_1$ is chosen from hydrogen, halogen, hydroxy, cyano, nitro, halo($C_1$–$C_6$)alkyl, halo($C_1$–$C_6$)alkoxy, $C_1$–$C_6$alkyl, $C_2$–$C_6$alkenyl, $C_2$–$C_6$alkynyl, $C_1$–$C_6$alkoxy, $C_3$–$C_7$cycloalkyl, ($C_3$–$C_7$cycloalkyl)$C_1$–$C_4$alkyl, mono- and di-amino($C_1$–$C_6$)alkyl, and —S(O)$_n$($C_1$–$C_6$)alkyl;

$R_2$ is $XR_C$ or Y;

$R_3$ is chosen from halo($C_1$–$C_6$)alkyl, halo($C_1$–$C_6$)alkoxy, $C_1$–$C_6$alkyl, $C_2$–$C_6$alkenyl, $C_2$–$C_6$alkynyl, $C_1$–$C_6$alkoxy, $C_3$–$C_7$cycloalkyl, ($C_3$–$C_7$cycloalkyl)$C_1$–$C_4$alkyl, mono- and di-amino($C_1$–$C_4$)alkyl, and —S(O)$_n$($C_1$–$C_6$)alkyl, —CH$_2$R$_C$, —CHR$_D$R$_C$, —OR$_C$, —C(=O)R$_C$, —NH$_D$R$_C$, —NR$_D$R$_C$, —C(=O)NHR$_C$, —C(=O)NR$_D$R$_C$, —S(O)$_n$NHR$_C$, —S(O)$_n$NR$_D$R$_C$, —NHC(=O)R$_C$, —NR$_D$C(=O)R$_C$, and Y;

$R_C$ and $R_D$, which may be the same or different, are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds, each of which 1 to 8 carbon atoms may be further substituted with one or more substituent(s) independently selected from hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z;

X is independently selected at each occurrence from the group consisting of —CH$_2$—, —CHR$_D$—, —O—, —C(=O)—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, —OSiH$_2$—, —OSiH($C_1$–$C_4$alkyl)-, —OSi($C_1$–$C_4$alkyl)($C_1$–$C_4$alkyl)-, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, $C_1$–$C_4$alkyl, —O($C_1$–$C_4$alkyl), —NH($C_1$–$C_4$alkyl), —N($C_1$–$C_4$alkyl)($C_1$–$C_4$alkyl), and —S(O)$_n$(alkyl), wherein said 3- to 7-memberered heterocyclic groups contain one or more heteroatom(s) independently selected from N, O, and S, with the point of attachment being either carbon or nitrogen; and n is independently selected at each occurrence from 0, 1, and 2.

36. A pharmaceutically acceptable salt comprising a cation of Formula I-b:

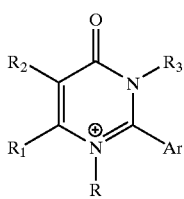

Formula I-b wherein:
Ar is chosen from phenyl optionally substituted with up to 5 groups R$_A$, naphthyl optionally substituted with up to 5 groups R$_A$, and heteroaryl optionally substituted with up to 5 groups R$_A$, said heteroaryl having from 1 to 3 rings, 5 to 7 ring members in each ring and, in at least one of said rings, from 1 to about 3 heteroatoms selected from the group consisting of N, O, and S;

R is methyl;

R$_1$ is chosen from hydrogen, halogen, hydroxy, cyano, nitro, haloalkyl, haloalkoxy, alkyl, alkenyl, alkynyl, alkoxy, cycloalkyl, (cycloalkyl)alkyl, mono- and di-aminoalkyl, and —S(O)$_n$alkyl;

R$_2$ is XR$_C$ or Y;

R$_3$ is chosen from haloalkyl, haloalkoxy, alkyl, alkenyl, alkynyl, alkoxy, cycloalkyl, (cycloalkyl)alkyl, mono- and di-, and —S(O)$_n$alkyl, —CH$_2$R$_C$, —CHR$_D$R$_C$, —OR$_C$, —C(=O)R$_C$, —NHR$_C$, —C(=O)NHR$_C$, —C(=O)NR$_D$R$_C$, —S(O)$_n$NHR$_C$, —S(O)$_n$NR$_D$R$_C$, —NHC(=O)R$_C$, —NR$_D$C(=O)R$_C$, and Y;

R$_A$ is independently selected at each occurrence from halogen, cyano, nitro, haloalkyl, haloalkoxy, hydroxy, amino, alkyl substituted with 0–2 R$_B$, alkenyl substituted with 0–2 R$_B$, alkynyl substituted with 0–2 R$_B$, cycloalkyl substituted with 0–2 R$_B$, (cycloalkyl)alkyl substituted with 0–2 R$_B$, alkoxy substituted with 0–2 R$_B$, —NH(alkyl) substituted with 0–2 R$_B$, —N(alkyl)(alkyl) of which each alkyl is independently substituted with 0–2 R$_B$, —XR$_C$, and Y;

R$_B$ is independently selected at each occurrence from the group consisting of halogen, hydroxy, cyano, amino, alkyl, —O(alkyl), —NH(alkyl), —N(alkyl)(alkyl), —S(O)$_n$(alkyl), haloalkyl, haloalkoxy, CO(alkyl), CONH(alkyl), CON(alkyl)(alkyl), —XR$_C$, and Y;

R$_C$ and R$_D$, which may be the same or different, are independently selected at each occurrence from:
hydrogen, and
straight, branched, and cyclic alkyl groups, and (cycloalkyl)alkyl groups, said straight, branched, and cyclic alkyl groups, and (cycloalkyl)alkyl groups consist of 1 to 8 carbon atoms, and contain zero or one or more double or triple bonds, each of which 1 to 8 carbon atoms may be further substituted with one or more substituent(s) independently selected from oxo, hydroxy, halogen, cyano, amino, $C_1$–$C_6$alkoxy, —NH($C_1$–$C_6$alkyl), —N($C_1$–$C_6$alkyl)($C_1$–$C_6$alkyl), —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z;

X is independently selected at each occurrence from the group consisting of —CH$_2$—, —CHR$_D$—, —O—, —C(=O)—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, —OSiH$_2$—, —OSiH($C_1$–$C_4$alkyl)-, —OSi($C_1$–$C_4$alkyl)($C_1$–$C_4$alkyl)-, and —NR$_D$S(O)$_n$—;

Y and Z are independently selected at each occurrence from: 3- to 7-membered carbocyclic or heterocyclic groups which are saturated, unsaturated, or aromatic, which may be further substituted with one or more substituents independently selected from halogen, oxo, hydroxy, amino, cyano, alkyl, —O(alkyl), —NH(alkyl), —N(alkyl)(alkyl), and —S(O)$_n$(alkyl), wherein said 3- to 7-memberered heterocyclic groups contain one or more heteroatom(s) independently selected from N, O, and S, with the point of attachment being either carbon or nitrogen; and n is independently selected at each occurrence from 0, 1, and 2;

provided that R$_1$ is not hydrogen, alkyl, or trifluoromethyl when R$_2$ is hydrogen, alkyl or alkenyl.

* * * * *